US007931903B2

(12) United States Patent
Hansen et al.

(10) Patent No.: US 7,931,903 B2
(45) Date of Patent: *Apr. 26, 2011

(54) INTERNALIZING ANTI-CD74 ANTIBODIES AND METHODS OF USE

(75) Inventors: Hans J. Hansen, Picayune, MS (US); Zhengxing Qu, Warren, NJ (US); David M. Goldenberg, Mendham, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/794,823

(22) Filed: Jun. 7, 2010

(65) Prior Publication Data

US 2010/0266497 A1 Oct. 21, 2010

Related U.S. Application Data

(60) Division of application No. 11/867,775, filed on Oct. 5, 2007, now Pat. No. 7,772,373, which is a continuation of application No. 10/377,122, filed on Mar. 3, 2003, now Pat. No. 7,312,318.

(60) Provisional application No. 60/360,259, filed on Mar. 1, 2002.

(51) Int. Cl.
*A61K 39/395* (2006.01)
(52) U.S. Cl. ............... 424/178.1; 424/183.1; 424/133.1; 424/138.1
(58) Field of Classification Search ......................... None
See application file for complete search history.

(56) References Cited

U.S. PATENT DOCUMENTS

| 4,816,567 | A | 3/1989 | Cabilly et al. |
| 5,618,920 | A | 4/1997 | Robinson et al. |
| 5,693,762 | A | 12/1997 | Queen et al. |
| 6,051,230 | A | 4/2000 | Thorpe et al. |
| 6,306,393 | B1 | 10/2001 | Goldenberg et al. |
| 6,653,104 | B2 | 11/2003 | Goldenberg et al. |
| 7,312,318 | B2 | 12/2007 | Hansen et al. |
| 7,585,491 | B2 | 9/2009 | Govindan |
| 2002/0018749 | A1 | 2/2002 | Hudson et al. |
| 2002/0041847 | A1 | 4/2002 | Goldenberg |
| 2003/0013122 | A1 | 1/2003 | Bucala et al. |

FOREIGN PATENT DOCUMENTS

| WO | 98/50435 | 11/1998 |
| WO | 00/67795 | 11/2000 |
| WO | 00/74718 | 12/2000 |

OTHER PUBLICATIONS

Bendig, M., "Humanization of Rodent Monoclonal Antibodies by CDR Grafting", Academic Press Inc., New York, NY, vol. 8, (1995), pp. 83-93.

Burgess et al., "Possible dissociation of the heparin-binding and mitogenic activities of heparin-binding (acidic fibroblast) growth factor-1 from its receptor-binding activities by site-directed mutagenesis of a single lysine residue", J. Cell Biol. 111:2129-2138 (1990).

Colman, P., "Effects of amino acid sequence changes on antibody-antigen interactions", Res. Immunol. 1994, 145:33-36.

Gondo et al., "HLA class II antigen associated invariant chain gene expression in malignant lymphoma", Br. J. Haematol. Dec. 1987;67(4):413-7.

Hansen et al., "Internalization and catabolism of radiolabelled antibodies to the MHC class-II invariant chain by B-cell lymphomas", Biochem. J. 1996, 320:293-300.

Ibragimova et al., "Stability of the beta-sheet of the WW domain: A molecular dynamics simulation study", Biophys. J. Oct. 1999;77(4):2191-8.

Kolata, G., "Clinical promise with new hormones", Science 236:517-519 (1987).

Lazar et al., "Transforming growth factor alpha: an aromatic side chain at position 38 is essential for biological activity", Mol. Cell. Biol. 8(3):1247-1252 (1988).

Leung et al., "Chimerization of LL2, a Rapidly Internalizing Antibody Specific for B Cell Lymphoma", Hybridoma 13 (6):469-76 (1994).

Leung et al., "Construction and characterization of a humanized, internalizing, B-cell (CD22)-specific leukemia/lymphoma antibody, LL2", Mol. Immunol. 32(17/18):1413-1427 (1995).

Moller et al., "CD74", J. Biol. Regul. Homeost. Agents Oct.-Dec. 2000;14(4):299-301.

Ochakovskaya et al., "Therapy of Disseminated B-Cell Lymphoma Xenografts in Severe Combined Immunodeficient Mice with an Anti-CD74 Antibody Conjugated with (111)Indium, (67)Gallium, or (90)Yttrium", Clin. Cancer Res. 7(6):1505-1510 (2001).

Orlandi et al., "Cloning immunoglobulin variable domains for expression by the polymerase chain reaction", Proc. Natl. Acad. Sci. USA 86:3833-3837 (1989).

Oster et al., "Erythropoietin for the Treatment of Anemia of Malignancy Associated with Neoplastic Bone Marrow Infiltration", J. Clin. Oncol., 8(6):956-962 (1990).

Qu et al., "Internalization and Cytotoxic Effects of a Humanized Anti-CD74 Antibody, LL1", Proc. Am. Assoc. Cancer Res 2002;43:255.

Rudikoff et al., "Single amino acid substitution altering antigen-binding specificity", Proc. Natl. Acad. Sci. USA 1982;79(6):1979-83.

(Continued)

*Primary Examiner* — Sheela J Huff
(74) *Attorney, Agent, or Firm* — Richard A. Nakashima

(57) ABSTRACT

The present invention provides humanized, chimeric and human anti-CD74 antibodies, CD74 antibody fusion proteins, immunoconjugates, vaccines and bispecific that bind to CD74, the major histocompatibility complex (MHC) class-II invariant chain, Ii, which is useful for the treatment and diagnosis of B-cell disorders, such as B-cell malignancies, other malignancies in which the cells are reactive with CD74, and autoimmune diseases, and methods of treatment and diagnosis.

38 Claims, 14 Drawing Sheets

OTHER PUBLICATIONS

Shih et al., "Localization of an antibody to CD74 (MHC class II invariant chain) to human B cell lymphoma xenografts in nude mice", Cancer Immunol. Immunother. 49:208-216 (2000).

Tutt et al., "Monoclonal Antibody Therapy of B Cell Lymphoma: Signaling Activity on Tumor Cells Appears More Important Than Recruitment of Effectors", J. Immunol. 161(6):3176-85 (1998).

FIG. 1A

```
CAGATCCAGTTGGTGCAGTCTGGACCTGAGCTGAAGAAGCCTGGAGAGACAGTCAAGGTCACCTGCAAGACTTCTGGATATACCTTCACA   90
----+----+----+----+----+----+----+----+----+----+----+----+----+----+----+----+----+----+
GTCTAGGTCAACCACGTCAGACCTGGACTCGACTTCTTCGGACCTCTCTGTCAGTTCCAGTGGACGTTCTGAAGACCTATATGGAAGTGT
 Q  I  Q  L  V  Q  S  G  P  E  L  K  K  P  G  E  T  V  K  V  T  C  K  T  S  G  Y  T  F  T
                 10                  20                  30

AACTATGGAGTGAACTGGATAAAGCAGACTCCAGGAGAGGGTTTACAGTGGATGGGCTGGATAAACCCAACACTGGAGAGCCAACATTT  180
----+----+----+----+----+----+----+----+----+----+----+----+----+----+----+----+----+----+
TTGATACCTCACTTGACCTATTTCGTCTGAGGTCCTCTCCCAAATGTCACCTACCCGACCTATTTGGGTTGTGACCTCTCGGTTGTAAA
 N  Y  G  V  N  W  I  K  Q  T  P  G  E  G  L  Q  W  M  G  W  I  N  P  N  T  G  E  P  T  F
       CDR1      40                  50    52A                      CDR2

GATGATGACTTCAAGGGACGATTTGCCTTCTCTTTGGAATCCTCTGCCAGCACTGCCTTTTTGCAGATCAGCAACCTCAAAAATGAGGAC  270
----+----+----+----+----+----+----+----+----+----+----+----+----+----+----+----+----+----+
CTACTACTGAAGTTCCCTGCTAAACGGAAGAGAAACCTTAGGAGACGGTCGTGACGGAAAAACGTCTAGTCGTTGGAGTTTTTACTCCTG
 D  D  D  F  K  G  R  F  A  F  S  L  E  S  S  A  S  T  A  F  L  Q  I  S  N  L  K  N  E  D
 60                    70                  80  82A B C
 CDR3

ATGGGTACATATTTCTGTTCAAGATCGAGGGGTAAAAACGAAGCCTGGTTTGCTTATTGGGGCCAAGGGACTCTGGTCACTGTCTCTGAA  360
----+----+----+----+----+----+----+----+----+----+----+----+----+----+----+----+----+----+
TACCCATGTATAAAGACAAGTTCTAGCTCCCCATTTTTGCTTCGGACCAAACGAATAACCCCGGTTCCCTGAGACCAGTGACAGAGACTT
 M  G  T  Y  F  C  S  R  S  R  G  K  N  E  A  W  F  A  Y  W  G  Q  G  T  L  V  T  V  S  E
         90          100A B K                         110
               CDR3
```

FIG. 1B

```
GATGTTGTGATGACCCAAACTCCACTCTCCCTGCCTGTCAGTCTTGGAGATCAAGCCTCCATCTCTTGCAGAGATCTAGTCAGAGCCTTGTA
----+----+----+----+----+----+----+----+----+----+----+----+----+----+----+----+----+----+  90
CTACAACACTACTGGGTTTGAGGTGAGAGGGACGGACAGTCAGAGTCTCTAGATCAGTCTCGGAACAT
                                                                                    27A B C
 D  V  V  M  T  Q  T  P  L  S  L  P  V  S  L  G  D  Q  A  S  I  S  C  R  S  S  Q  S  L  V
                   10                      20                                   
                                                                         CDR1

CACAGAAATGGAAACACCTATTTACATTGGTACCTGCAGAAGCCAGGCCAGTCTCCAAAGCTCCTGATCTACACAGTTTCCAACCGATTT
----+----+----+----+----+----+----+----+----+----+----+----+----+----+----+----+----+----+ 180
GTGTCTTTACCTTTGTGGATAAATGTAACCATGGACGTCTTCGGTCCGGTCAGAGGTTTCGAGGACTAGATGTGTCAAAGGTTGGCTAAA
 D  E  H  R  N  T  Y  L  H  W  Y  L  Q  K  P  G  Q  S  P  K  L  L  I  Y  T  V  S  N  R  F
         30                      40                      50
       CDR1                                                       CDR2

TCTGGGGTCCCAGACAGGTTCAGTGGCAGTGGATCAGGGACAGATTTCACACTCAAGATCAGTAGAGTGGAGGCTGAGGATCTGGGACTT
----+----+----+----+----+----+----+----+----+----+----+----+----+----+----+----+----+----+ 270
AGACCCCAGGGTCTGTCCAAGTCACCGTCACCTAGTCCCTGTCTAAAGTGTGAGTTCTAGTCATCTCAGCTCCGACTCCTAGACCCTGAA
 S  G  V  P  D  R  F  S  G  S  G  S  G  T  D  F  T  L  K  I  S  R  V  E  A  E  D  L  G  L
                      60                      70                      80

TATTTCTGCTCTCAAAGTTCACATGTTCCTCCCACGTTCGGTGCTGGGACCAAGCTGGAGATCTAAC
----+----+----+----+----+----+----+----+----+----+----+----+----+-- 337
ATAAAGACGAGAGTTTCAAGTGTACAAGGAGGGTGCAAGCCACGACCCTGGTTCGACCTCTAGATTG
                                         100
 Y  F  C  S  Q  S  S  H  V  P  P  T  F  G  A  G  T  K  L  E  I
              90
       CDR3
```

FIG. 2A

```
                  PstI
CAGGTCCAACTGCAG CAGTCTGGACCTGAGCTGAAGAAGCCTGGAGAGACAGTCAAGGTCACCTGCAAGACTTCTGGATATACCTTCACA    90
---------------+---------------+---------------+---------------+---------------+----------
GTCCAGGTTGACGTC GTCAGACCTGGACTCGACTTCTTCGGACCTCTCTGTCAGTTCCAGTGGACGTTCTGAAGACCTATATGGAAGTGT

Q  V  Q  L  Q  Q  S  G  P  E  L  K  K  P  G  E  T  V  K  V  T  C  K  T  S  G  Y  T  F  T    30

AACTATGGAGTGAACTGGATAAAGCAGACTCCAGGAGAGGGTTTACAGTGGATGGGCTGGATAAACCCCAACACTGGAGAGCCAACATTT   180
---------------+---------------+---------------+---------------+---------------+----------
TTGATACCTCACTTGACCTATTTCGTCTGAGGTCCTCTCCCAAATGTCACCTACCCGACCTATTTGGGGTTGTGACCTCTCGGTTGTAAA

N  Y  G  V  N  W  I  K  Q  T  P  G  E  G  L  Q  W  M  G  W  I  N  P  N  T  G  E  P  T  F    59
 ‾‾‾‾‾‾‾‾‾‾‾‾‾                                       ‾‾‾‾‾‾‾‾‾‾‾‾‾‾‾‾‾‾‾‾‾‾‾‾‾‾‾‾‾‾‾‾‾‾‾‾‾
     CDR1                                                          CDR2

GATGATGACTTCAAGGGACGATTTGCCTTCTCTTTGGAATCCTCTGCCAGCACTGCCTTTTTGCAGATCAGCAACCTCAAAAATGAGGAC   270
---------------+---------------+---------------+---------------+---------------+----------
CTACTACTGAAGTTCCCTGCTAAACGGAAGAGAAACCTTAGGAGACGGTCGTGACGGAAAAACGTCTAGTCGTTGGAGTTTTTACTCCTG

D  D  D  F  K  G  R  F  A  F  S  L  E  S  S  A  S  T  A  F  L  Q  I  S  N  L  K  N  E  D    89
 ‾‾‾‾‾‾‾‾‾‾‾‾‾

BstEII
ATGGGTACATATTTCTGTTCAAGATCGAGGGGTAAAAACGAAGCCTGGTTTGCTTATTGGGGCCAAGGA CTCGGTCACC CTCTCCTCA   360
---------------+---------------+---------------+---------------+---------------+----------
TACCCATGTATAAAGACAAGTTCTAGCTCCCCATTTTTGCTTCGGACCAAACGAATAACCCCGGTTCCT GAGCCAGTGG GAGAGGAGT

M  G  T  Y  F  C  S  R  S  R  G  K  N  E  A  W  F  A  Y  W  G  Q  G  T  L  V  T  V  S  S    113
                 ‾‾‾‾‾‾‾‾‾‾‾‾‾‾‾‾‾‾‾‾‾‾‾‾‾‾‾‾‾‾‾‾‾‾‾‾‾‾‾‾‾‾
                                  CDR3
```

FIG. 2B

```
         PvuII
GACATCCAGCTGACCCAAACTCCCACTCTCCCTGCCTGTCAGTCTTGGAGATCAAGCCTCCATCTCTTGCAGATCTAGTCAGAGCCTTGTA    90
----+----+----+----+----+----+----+----+----+----+----+----+----+----+----+----+----+----+
CTGTAGGTCGACTGGGTTTGAGGGTGAGAGGGACGGACAGTCAGAACCTCTAGTTCGGAGGTAGAGAACGTCTAGATCAGTCTCGGAACAT
      D   I   Q   L   T   Q   T   P   L   S   L   P   V   S   L   G   D   Q   A   S   I   S   C   R   S   S   Q   S   L   V    27C

CACAGAAATGGAAACACCTATTTACATTGGTACCTGCAGAAGCCAGGCCAGTCTCCTCAAAGCTCCTGATCTACACAGTTTCCAACCGATTT   180
----+----+----+----+----+----+----+----+----+----+----+----+----+----+----+----+----+----+
GTGTCTTTACCTTTGTGGATAAATGTAACCATGGACGTCTTCGGTCCGGTCAGAGGAGTTTCGAGGACTAGATGTGTCAAAGGTTGGCTAAA
  H   R   N   G   N   T   Y   L   H   W   Y   L   Q   K   P   G   Q   S   P   K   L   L   I   Y   T   V   S   N   R   F    55
  CDR1                                                                                 CDR2

TCTGGGGTCCCAGACAGGTTCAGTGGCAGTGGATCAGGGACAGATTTCACACTCAAGATCAGTAGAGTGGAGGCTGAGGATCTGGGACTT   270
----+----+----+----+----+----+----+----+----+----+----+----+----+----+----+----+----+----+
AGACCCCAGGGTCTGTCCAAGTCACCGTCACCTAGTCCCTGTCTAAAGTGTGAGTTCTAGTCATCTCACCTCCGACTCCTAGACCCTGAA
  S   G   V   P   D   R   F   S   G   S   G   S   G   T   D   F   T   L   K   I   S   R   V   E   A   E   D   L   G   L    85

BglII/BclI
TATTTCTGCTCTCAAAGTTCACATGTTCCTCCCACGTTCGGTGCTGGGACCAAGCTGGAGATCAAACGT   339
----+----+----+----+----+----+----+----+----+----+----+----+----+----
ATAAAGACGAGAGTTTCAAGTGTACAAGGAGGGTGCAAGCCACGACCCTGGTTCGACCTCTAGTTTGCA
  Y   F   C   S   Q   S   S   H   V   P   P   T   F   G   A   G   T   K   L   E   I   K   R    108
              CDR3
```

```
RF-TS3   QVQLVQSGSELKKPGASVKVSCKASGYTFT SYAMN WVRQA    40
cLL1VH   QVQLQ····P······ET···T·······  N·GV··IK·T    40
hL1VH    QVQLQ···················· ····  N·GV··IK·T    40

RF-TS3   PGQGLEWMG WINTNTGNPTYAQGFTG RFVFSLDTSVSTAY     79
cLL1VH   ··E···Q····· P··E··FDDD·K ···A···ES·A··F     79
hL1VH    ······Q····· ···· P··E··FDDD·K ···A·········  79

RF-TS3   LQISSLKADDTAVYYCAR EDSNGYKIFDY                102
cLL1VH   ····N··NE·MGT·F·S· SRGKNEAW·A·                102
hL1VH    ···············F·S· SRGKNEAW·A·              102

NE

```
HF-21/28   DVVMTQSPLSLPVTLGQPASISCRSSQSLVHSDGNTYLNW   35
cLL1Vk     DIQL··T······S·GDQ··········RN·····H·     35
hLL1Vk     DIQL················· ······RN·····H·     35

HF-21/28   FQQRPGQSPRRLIYKVSNRDSGVPDRFSGSGSGTDFTLKI   75
cLL1Vk     YL·K····KL···T·····F···················   75
hLL1Vk     ········L···T·····F···················   75

HF-21/28   SRVEAEDVGVYYCMQGTHWPFTFGQGTRLEI          106
cLL1Vk     ·············L·F·SS·V·P···A··K··IKR     108
hLL1Vk     ·············F·SS·V·P···A······IKR     108
```

• denotes the amino acid is identical to the one shown in the first row

FIG.3B hLL1VH

```
CAGGTCCAACTGCAGCAATCTGGGTCTGAGTTGAAGAAGCCTGGGGCCTCAGTGAAGGTTCCTGCAAGGCTTCACT          90
---------+---------+---------+---------+---------+---------+
GTCCAGGTTGACGTCGTTAGACCCAGACTCAACTTCTTCGGACCCCGGAGTCACTTCCAAGGACGTTCCGAAGACCTATGTGGAAGTGA

Q  V  Q  L  Q  Q  S  G  S  E  L  K  K  P  G  A  S  V  K  V  S  C  K  A  S  G  Y  T  F  T      30
```

```
AACTATGGAGTGAACTGGATAAAGCAGGCCCCTGGACAAGGGCTTGAGTGGATGGGCTGGATAAACCCCAACACTGGAGAGCCAACATTT    180
---------+---------+---------+---------+---------+---------+
TTGATACCTCACTTGACCTATTTCGTCCGGGGACCTGTTCCCGAACTCACCTACCCGACCTATTTGGGGTTGTGACCTCTCGGTTGTAAA

N  Y  G  V  N  W  I  K  Q  A  P  G  Q  G  L  Q  W  M  G  W  I  N  P  N  T  G  E  P  T  F      59
 ───CDR1───                                           ─────────CDR2─────────
```

```
GATGATGACTTCAAGGGACGATTTGCCTTCTCCCTTGGACACCTCTGTCAGCACGGCATATCTCCAGATCAGCAGCCTAAAGGCTGACGAC    270
---------+---------+---------+---------+---------+---------+
CTACTACTGAAGTTCCCTGCTAAACGGAAGAGGGAACCTGTGGAGACAGTCGTGCCGTATAGAGGTCTAGTCGTCGGATTTCCGACTGCTG

D  D  D  F  K  G  R  F  A  F  S  L  D  T  S  V  S  T  A  Y  L  Q  I  S  S  L  K  A  D  D      89
 ───CDR3───
```

```
ACTGCCGTGTATTTCTGTTCAAGATCGAGGGGTAAAAACGAAGCCTGGTTTGCTTATTGGGGCCAAGGGAGCCTGGTCACCGTCTCCTCA    360
---------+---------+---------+---------+---------+---------+
TGACGGCACATAAAGACAAGTTCTAGCTCCCCATTTTGCTTCGGACCAAACGAATAACCCCGGTTCCCTCGGACCAGTGGCAGAGGAGT

T  A  V  Y  F  C  S  R  S  R  G  K  N  E  A  W  F  A  Y  W  G  Q  G  S  L  V  T  V  S  S     113
                    ─────────CDR3─────────
```

```
GACATCCAGCTGACTCAGTCTCCACTCTCCCTGCCCGTCACCCTTGGACAGCCGGCCTCCATCTCCTGCAGATCAAGTCAGAGCCTTGTA        90
---------+---------+---------+---------+---------+---------+---------+---------+---------+
CTGTAGGTCGACTGAGTCAGAGATGGGAGGGCAGGGCAGTGGGAACCTGTCGGCCGGAGGTAGAGGACGTCTAGTTCAGTCTCGGAACAT       280
 D  I  Q  L  T  Q  S  P  L  S  L  P  V  T  L  G  Q  P  A  S  I  S  C  R  S  S  Q  S  L  V
                                                                      CDR1

CACAGAAATGGAAACACCTATTTACATTGGTTTCAGCAGAGGCCAGGCCAATCTCCAAGGCTCCTGATCTACACAGTTTCCAACCGATTT       180
---------+---------+---------+---------+---------+---------+---------+---------+---------+
GTGTCTTTACCTTTGTGGATAAATGTAACCAAAGTCGTCTCCGGTCCGGTTAGAGGTTCCGAGGACTAGATGTGTCAAAGGTTGGCTAAA        55
 H  R  N  G  N  T  Y  L  H  W  F  Q  Q  R  P  G  Q  S  P  R  L  L  I  Y  T  V  S  N  R  F
        CDR1                                                              CDR2

TCTGGGGTCCCAGACAGATTCAGCGGCAGTGGGTCAGGCACTGATTTCACACTGAAAATCAGCAGGGTGGAGGCTGAGGATGTTGGGGTT       270
---------+---------+---------+---------+---------+---------+---------+---------+---------+
AGACCCCAGGGTCTGTCTAAGTCGCCGTCACCCAGTCCGTGACTAAAGTGTGACTTTTAGTCGTCCCACCTCCGACTCCTACAACCCCAA        85
 S  G  V  P  D  R  F  S  G  S  G  S  G  T  D  F  T  L  K  I  S  R  V  E  A  E  D  V  G  V

TATTTCTGCTCTCAAAGTTCACATGTTCCTCCCACGTTCGGTGCTGGGACCACGACTGGAGATCAAACGT                         339
---------+---------+---------+---------+---------+---------+---------+
ATAAAGACGAGAGTTTCAAGTGTACAAGGAGGGTGCAAGCCACGACCCTGGTGCTGACCTCTAGTTTGCA                         108
 Y  F  C  S  Q  S  S  H  V  P  P  T  F  G  A  G  T  R  L  E  I  K  R
           CDR3
```

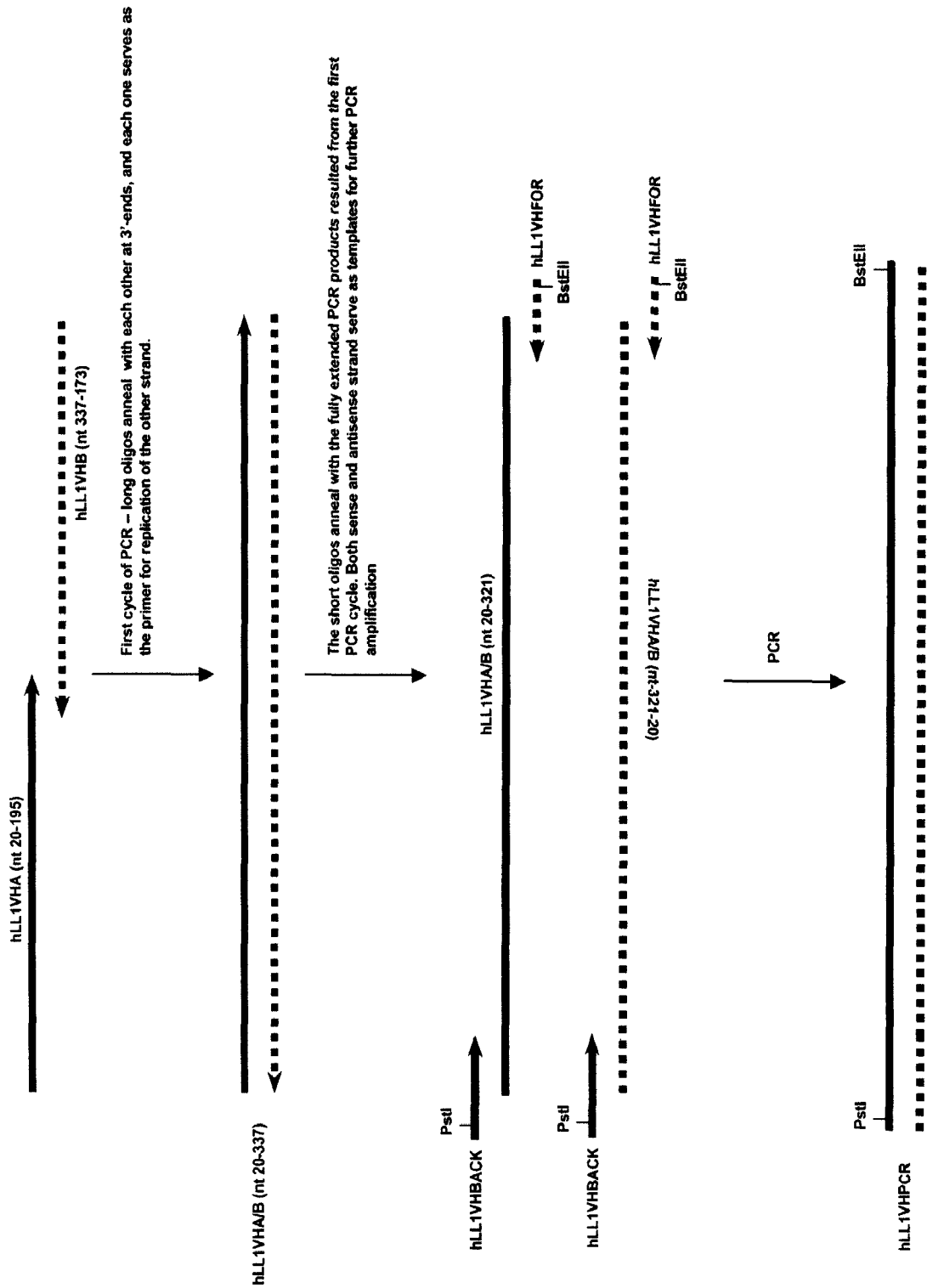

INTERNALIZING ANTI-CD74 ANTIBODIES AND METHODS OF USE

This application is a divisional of U.S. Ser. No. 11/867,775 (Publ. No. 20080166342), filed Oct. 5, 2007, which is a continuation of U.S. Ser. No. 10/377,122 (now issued U.S. Pat. No. 7,312,318), filed Mar. 3, 2003, which claimed the benefit under 35 U.S.C. §119(e) of U.S. Provisional Application No. 60/360,259, filed Mar. 1, 2002, each of which is incorporated herein by reference in its entirety.

SEQUENCE LISTING

The instant application contains a Sequence Listing which has been submitted via EFS-Web and is hereby incorporated by reference in its entirety. Said ASCII copy, created on Dec. 17, 2010, is name IMM171UStxt, and is 25,524 bytes in size.

BACKGROUND OF THE INVENTION

1. Field of the Invention

The present invention relates to humanized, chimeric and human anti-CD74 antibodies or fragments thereof or antibody fusion proteins comprising at least one anti-CD74 antibody, particularly monoclonal antibodies (mAbs), therapeutic and diagnostic conjugates of humanized, chimeric and human anti-CD74 mAbs or fragments thereof, and methods of treating and diagnosing B cell lymphomas and leukemias, malignancies other than lymphomas and leukemias in which the cells are positive for the CD74 antigen and various autoimmune and immune dysregulation diseases using these humanized, chimeric and human anti-CD74 mAbs or fragments thereof. The present invention relates to multivalent and/or multispecific anti-CD74 mAbs or fragments thereof comprising at least one arm of an anti-CD74 mAb or fragment thereof and at least one arm of the multispecific mAb to a noxious substance, such as a pathogenic organism, such as a cancer cell, a parasite or an infectious agent. The present invention further relates to an anti-CD74 mAb or fragment thereof conjugated to an antigenic peptide. The humanized, chimeric and human anti-CD74 mAbs, fragments thereof, and conjugates thereof may be administered alone or as part of a multimodal therapeutic regimen. The present invention relates to DNA sequences encoding humanized, chimeric and human anti-CD74 antibodies, and multivalent and/or multispecific anti-CD74 mAbs and fragments thereof, and therapeutic, diagnostic and antigenic conjugates thereof, vectors and host cells containing the DNA sequences, and methods of making the humanized, chimeric and human anti-CD74 antibodies.

2. Background

One of the major goals of immunotherapy is to harness a patient's immune system against tumor cells or infectious organisms. With regard to cancer therapy, the object is to direct the patient's immune system against tumor cells. Non-Hodgkins lymphoma (NHL), multiple myeloma, and chronic and acute lymphocytic leukemia are B-cell malignancies that remain important contributors to cancer mortality. The response of these malignancies to various forms of treatment is mixed.

Induction of a T-lymphocyte response is a critical initial step in a host's immune response. Activation of T cells results in T cell proliferation, cytokine production by T cells and generation of T cell-mediated effector functions. T-cell activation requires an antigen-specific signal, often called a primary activation signal, which results from stimulation of a clonally-distributed T cell receptor (TcR) present on the surface of the T cell. This antigen-specific signal is usually in the form of an antigenic peptide bound either to a major histocompatibility complex (MHC) class I protein or an MHC class II protein present on the surface of an antigen-presenting cell (APC). The MHC molecules in humans are designated as HLA (human leukocyte antigen) molecules.

Class-II molecules are found on a limited number of cell types, primarily B cells, monocytes/macrophages and dendritic cells, and, in most cases, present peptides derived from proteins taken up from the extracellular environment. MHC class-II are charged in cellular compartments which communicate with the extracellular environment. In humans the MHC-II molecules comprise the HLA-DR, HLA-DQ and HLA-DP molecules, which occur in various genetically coded alleles. Thus, e.g., bacterial antigens from the extracellular environment can be taken up and be presented after intracellular processing in the antigen-presenting cells on their cell surface. CD4+ T cells recognize peptides associated with class-II molecules.

The use of targeting monoclonal antibodies conjugated to radionuclides or other cytotoxic agents offers the possibility of delivering such agents directly to the tumor site, thereby limiting the exposure of normal tissues to toxic agents (Goldenberg, *Semin. Nucl. Med.,* 19: 332 (1989)). In recent years, the potential of antibody-based therapy and its accuracy in the localization of tumor-associated antigens have been demonstrated both in the laboratory and clinical studies (see, e.g., Thorpe, *TIBTECH,* 11: 42 (1993); Goldenberg, *Scientific American*, Science & Medicine, 1: 64 (1994); Baldwin et al., U.S. Pat. Nos. 4,925,922 and 4,916,213; Young, U.S. Pat. No. 4,918,163; U.S. Pat. No. 5,204,095; Irie et al., U.S. Pat. No. 5,196,337; Hellstrom et al., U.S. Pat. No. 5,134,075 and U.S. Pat. No. 5,171,665). In general, the use of radio-labeled antibodies or antibody fragments against tumor-associated markers for localization of tumors has been more successful than for therapy, in part because antibody uptake by the tumor is generally low, ranging from only 0.01% to 0.001% of the total dose injected (Vaughan et al., *Brit. J. Radiol.,* 60: 567 (1987)). Increasing the concentration of the radiolabel to increase the dosage to the tumor is counterproductive, generally, as this also increases exposure of healthy tissue to radioactivity.

Murine LL1 (mLL1 or murine anti-CD74 antibody) is a specific monoclonal antibody (mAb) reactive with CD74, the HLA Class-II-like antigen, i.e., the invariant chain (Ii determinant) on the surface of B-lymphocytes, monocytes and histiocytes, human B-lymphoma cell lines, melanomas, T-cell lymphomas and a variety of other tumor cell types (Hansen et al., *Biochem. J.* 320:293 (1996)). Cell surface-bound LL1 is rapidly internalized to the lysosomal compartment and quickly catabolized, much faster than other mAbs, such as anti-CD19 and anti-CD22. Id. This inherent property of LL1 overcomes some of the aforementioned difficulties with immunotherapy.

Murine LL1 was developed by fusion of mouse myeloma cells with splenocytes from BALB/c mice immunized with preparations from the Raji B-lymphoma cell line (called EPB-1 in Pawlak-Byczkowska et al., *Can. Res.,* 49: 4568 (1989)). The clinical use of mLL1, just as with most other promising murine antibodies, has been limited by the development in humans of a human anti-mouse antibody (HAMA) response. A HAMA response is generally not observed following injection of mLL1 Fab', as evidenced in a bone marrow imaging study using a mLL1 Fab' labeled with $^{99m}$Tc. Juweid et. al., *Nuc. Med. Camm.* 18: 142-148 (1997). However, in some therapeutic and diagnostic uses, a full-length anti-CD74 mAb may be preferred. This use of the full-length anti-CD74 mAb can limit the diagnostic and therapeutic usefulness of such antibodies and antibody conjugates, not only because of the potential anaphylactic problem, but also as a major portion of the circulating conjugate may be complexed to and sequestered by the circulating anti-mouse antibodies. Although the use of antibody fragments of mLL1 may circumvent the problems of immunogenicity, there are circumstances in which whole IgG is more desirable and the induction of cellular immunity is intended for therapy or enhanced antibody survival time. In general, HAMA responses pose a potential obstacle to realizing the full diagnostic and therapeutic potential of murine anti-CD74 mAbs. Therefore, the development of chimeric, humanized and human anti-CD74 mAbs and fragments thereof, antibody fusion proteins thereof and fragments thereof, immunoconjugates for therapy and diagnosis, multivalent and/or multispecific mAbs, and fragments thereof and vaccine conjugates thereof would be extremely useful for therapy and diagnosis, with reduced production of human anti-mouse antibodies.

SUMMARY OF THE INVENTION

The present invention is directed to anti-CD74 antibodies and fragments thereof and antibody fusion proteins thereof, particularly chimeric, humanized or human antibodies, which can be rapidly internalized into a cell.

The present invention is further directed to anti-CD74 antibody fusion proteins containing antibodies or fragments thereof that are fused to each other and/or to other antibodies and fragments thereof of the present invention.

The present invention additionally is directed to immunoconjugates containing the anti-CD74 antibodies or fragments thereof or the antibody fusion proteins or fragments thereof of the present invention linked to a diagnostic or therapeutic agent.

The present invention also is directed to a vaccine comprising an antibody conjugate containing the anti-CD74 antibodies or fragments thereof or the antibody fusion proteins or fragments thereof of the present invention linked to antigenic peptides.

The present invention further is directed to a bispecific or multispecific antibody comprising an antibody conjugate containing the anti-CD74 antibodies or fragments thereof or the antibody fusion proteins or fragments thereof of the present invention linked to an antibody or antibody fragment specific for a cancer marker substance, an epitope on the surface of an infectious disease organism or a noxious substance in the blood or other body fluid.

The present invention is additionally directed to methods of treating and diagnosing diseases using the CD74 antibodies and fragments thereof or antibody fusion proteins thereof and conjugates thereof of the present invention.

The present invention also is directed to DNA sequences encoding the CD74 antibodies or fragments thereof or antibody fusion proteins or fragments thereof, immunoconjugates and antibody conjugates and multispecific antibodies thereof, expression vectors and host cells containing the DNA sequences, and methods of expressing these CD74 antibodies of the present invention.

BRIEF DESCRIPTION OF THE FIGURES

FIG. 1 shows the DNA and amino acid sequences of the murine LL1 heavy and light chain variable regions. FIG. 1A shows the DNA (SEQ ID NO:1) and amino acid (SEQ ID NO:2) sequences of the LL1 VH obtained by RT-PCR. FIG. 1B shows the DNA (SEQ ID NO:3) and amino acid (SEQ ID NO:4) sequences of the LL1Vk obtained by 5'-RACE. Amino acid sequences encoded by the corresponding DNA sequences are given as one-letter codes below the nucleotide sequence. Numbering of the nucleotide sequences is on the right side. The amino acid residues in the CDR regions are shown in bold and underlined. Kabat's Ig molecule numbering is used for amino acid residues as shown by the numbering above the amino acid residues. The residues numbered by a letter following a particular digit indicates the insertion residues defined by Kabat numbering scheme. The insertion residues numbered with a letter have the same preceding digit. For example, residues 82A, 82B and 82C in FIG. 1A are indicated as 82A, B, and C.

FIG. 2 shows the DNA and amino acid sequences of the chimeric LL1 (cLL1) heavy and light chain variable regions expressed in Sp2/0 cells. FIG. 2A shows the DNA (SEQ ID NO:5) and amino acid (SEQ ID NO:6) sequences of the cLL1VH. FIG. 2B shows the double-stranded DNA (SEQ ID NO:7) and amino acid (SEQ ID NO:8) sequences of the cLL1Vk. Amino acid sequences encoded by the corresponding DNA sequences are given as one-letter codes. The amino acid residues in the CDR regions are shown in bold and underlined. The numbering of nucleotides and amino acids is same as that in FIG. 1. The restriction sites used for constructing the cLL1 are boxed and indicated.

FIG. 3 shows the alignment of the amino acid sequences of light and heavy chain variable regions of a human antibody, cLL1 and hLL1. FIG. 3A shows the VH amino acid sequence alignment of the human antibody RF-TS3, (SEQ ID NO:9) cLL1 (SEQ ID NO:6) and hLL1 (SEQ ID NO:11) and FIG. 3B shows the Vk amino acid sequence alignment of the human antibody HF-21/28, (SEQ ID NO:12) cLL1 (SEQ ID NO:8) and hLL1 (SEQ ID NO:14). Dots indicate the residues in cLL1 that are identical to the corresponding residues in the human antibodies. Boxed regions preprent the CDR regions. Both N- and C-terminal residues (underlined) of cLL1 are fixed by the staging vectors used and not compared with the human antibodies. Kabat's Ig molecule number scheme is used as in FIG. 1.

FIG. 4 shows the DNA and amino acid sequences of the humanized LL1 (hLL1) heavy and light chain variable regions expressed in Sp2/0 cells. FIG. 4A shows the DNA (SEQ ID NO:10) and amino acid (SEQ ID NO:11) sequences of the hLL1VH and FIG. 4B shows the DNA (SEQ ID NO:13) and amino acid (SEQ ID NO:14) sequences of the hLL1Vk. Amino acid sequences encoded by the corresponding DNA sequences are given as one letter codes. The amino acid residues in the CDR regions are shown in bold and underlined. Kabat's Ig molecule numbering scheme is used for amino acid residues as in FIG. 1A and FIG. 1B.

FIG. 5 shows a schematic diagram of construction of hLL1VH gene. Oligos used as templates and primers are shown as arrow lines. The arrow heads indicate the 3'-ends. The sense DNA strands (templates, primers and PCR products) are shown in solid lines and the anti-sense strands in doted lines. The Vk gene was similarly constructed.

FIG. 8A shows the fate of the bound Ab followed for up to 3 days. FIG. 8B shows the result of hLL1 processing studied at early time points (less than 3 h). The data was averaged of two experiments.

DETAILED DESCRIPTION OF THE INVENTION

Figure 6:
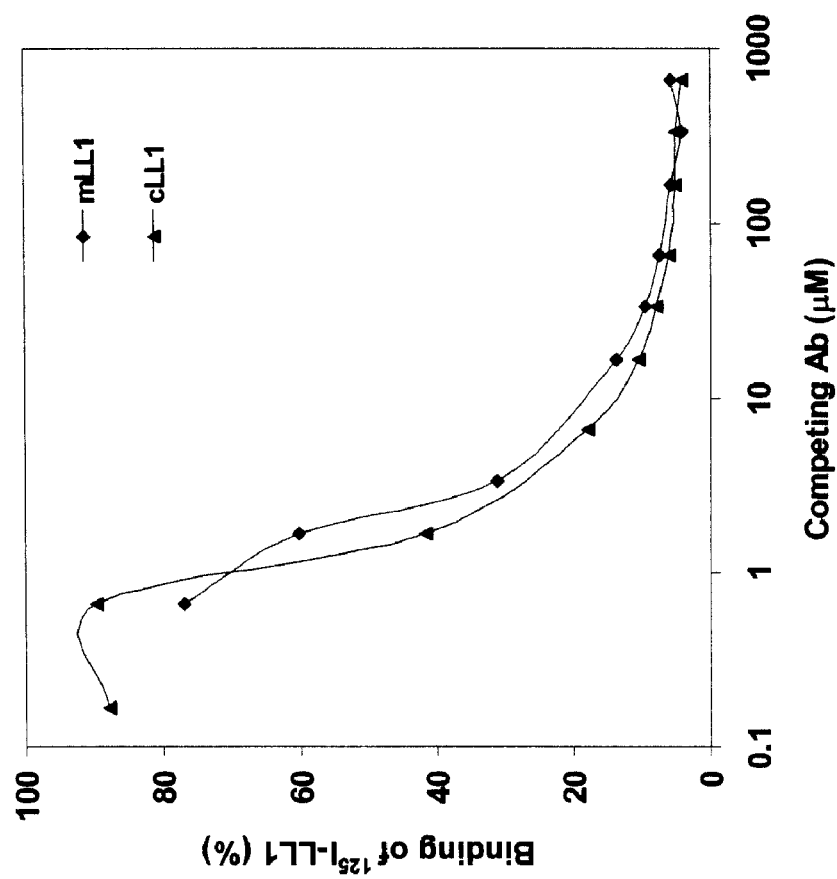
FIG. 6 shows the result of a competitive cell surface binding assay to compare the binding affinity of cLL1 with that of murine LL1. Varying concentrations of cLL1 (triangles) or mLL1 (diamonds) were mixed with a constant amount of $^{125}$I-labeled mLL1 and incubated with Raji cells at 4° C. for 1 h. The cell surface bound radiolabeled mLL1 was counted after washing. cLL1 and the murine LL1 competed equally well for the binding of radiolabeled LL1 to Raji cells, confirming the cloned V genes are authentic.

Unless otherwise specified, the terms "a" or "an" mean "one or more."

Overview

The present invention provides a humanized, a chimeric and a human anti-CD74 mAb, fragments thereof, an antibody fusion protein, and therapeutic and diagnostic conjugates thereof useful for treatment of mammalian subjects, humans and domestic animals, alone, as a conjugate or administered in combination with other therapeutic agents, including other naked antibodies and antibody therapeutic conjugates as part of a multimodal therapy regimen. Methods of treatment and diagnosis of B-cell malignancies, other CD74 positive malignancies and autoimmune diseases are disclosed.

DEFINITIONS

In the description that follows, a number of terms are used and the following definitions are provided to facilitate understanding of the present invention.

An antibody, as described herein, refers to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

An antibody fragment is a portion of an antibody such as F(ab')$_2$, F(ab)$_2$, Fab', Fab, Fv, sFv and the like. Regardless of structure, an antibody fragment binds with the same antigen that is recognized by the intact antibody. For example, an anti-CD74 monoclonal antibody fragment binds with an epitope of CD74. The term "antibody fragment" also includes any synthetic or genetically engineered protein that acts like an antibody by binding to a specific antigen to form a complex. For example, antibody fragments include isolated fragments consisting of the variable regions, such as the "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

A naked antibody is generally an entire antibody that is not conjugated to a therapeutic agent. This is so because the Fc portion of the antibody molecule provides effector functions, such as complement fixation and ADCC (antibody dependent cell cytotoxicity) that set mechanisms into action that may result in cell lysis. However, it is possible that the Fc portion is not required for therapeutic function, with other mechanisms, such as apoptosis, coming into play. Naked antibodies include both polyclonal and monoclonal antibodies, as well as certain recombinant antibodies, such as chimeric, humanized or human antibodies.

A chimeric antibody is a recombinant protein that contains the variable domains including the complementarity determining regions (CDRs) of an antibody derived from one species, preferably a rodent antibody, while the constant domains of the antibody molecule is derived from those of a human antibody. For veterinary applications, the constant domains of the chimeric antibody may be derived from that of other species, such as a cat or dog.

A humanized antibody is a recombinant protein in which the CDRs from an antibody from one species; e.g., a rodent antibody, is transferred from the heavy and light variable chains of the rodent antibody into human heavy and light variable domains. The constant domains of the antibody molecule is derived from those of a human antibody.

A human antibody is an antibody obtained from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13 (1994), Lonberg et al., *Nature* 368:856 (1994), and Taylor et al., *Int. Immun.* 6:579 (1994). A fully human antibody also can be constructed by genetic or chromosomal transfection methods, as well as phage display technology, all of which are known in the art. See for example, McCafferty et al., *Nature* 348:552-553 (1990) for the production of human antibodies and fragments thereof in vitro, from immunoglobulin variable domain gene repertoires from unimmunized donors. In this technique, antibody variable domain genes are cloned in-frame into either a major or minor coat protein gene of a filamentous bacteriophage, and displayed as functional antibody fragments on the surface of the phage particle.

Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see e.g. Johnson and Chiswell, *Current Opinion in Structural Biology* 3:5564-571 (1993).

Human antibodies may also be generated by in vitro activated B cells. See U.S. Pat. Nos. 5,567,610 and 5,229,275, which are incorporated in their entirety by reference.

A therapeutic agent is a molecule or atom which is administered separately, concurrently or sequentially with an antibody moiety or conjugated to an antibody moiety, i.e., antibody or antibody fragment, or a subfragment, and is useful in the treatment of a disease. Examples of therapeutic agents include antibodies, antibody fragments, drugs, toxins, enzymes, nucleases, hormones, immunomodulators, antisense oligonucleotides, chelators, boron compounds, photoactive agents or dyes and radioisotopes.

A diagnostic agent is a molecule or atom which is administered conjugated to an antibody moiety, i.e., antibody or antibody fragment, or subfragment, and is useful in diagnosing a disease by locating the cells containing the antigen. Useful diagnostic agents include, but are not limited to, radioisotopes, dyes (such as with the biotin-streptavidin complex), contrast agents, fluorescent compounds or molecules and enhancing agents (e.g., paramagnetic ions) for magnetic resonance imaging (MRI). U.S. Pat. No. 6,331,175 describes MRI technique and the preparation of antibodies conjugated to a MRI enhancing agent and is incorporated in its entirety by reference. Preferably, the diagnostic agents are selected from the group consisting of radioisotopes, enhancing agents for use in magnetic resonance imaging, and fluorescent compounds. In order to load an antibody component with radioactive metals or paramagnetic ions, it may be necessary to react it with a reagent having a long tail to which are attached a multiplicity of chelating groups for binding the ions. Such a tail can be a polymer such as a polylysine, polysaccharide, or other derivatized or derivatizable chain having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose. Chelates are coupled to the peptide antigens using standard chemistries. The chelate is normally linked to the antibody by a group which enables formation of a bond to the molecule with minimal loss of immunoreactivity and minimal aggregation and/or internal cross-linking. Other, more unusual, methods and reagents for conjugating chelates to antibodies are disclosed in U.S. Pat. No. 4,824,659 to Hawthorne, entitled "Antibody Conjugates", issued Apr. 25, 1989, the disclosure of which is incorporated herein in its entirety by reference. Particularly useful metal-chelate combinations include 2-benzyl-DTPA and its monomethyl and cyclohexyl analogs, used with diagnostic isotopes in the general energy range of 60 to 4,000 keV, such as $^{125}I$, $^{131}I$, $^{123}I$, $^{124}I$, $^{62}CU$, $^{64}CU$, $^{18}F$, $^{111}In$, $^{67}Ga$, $^{68}Ga$, $^{99m}Tc$, $^{94m}Tc$, $^{11}C$, $^{13}N$, $^{15}O$, $^{76}Br$, for radio-imaging. The same chelates, when complexed with non-radioactive metals, such as manganese, iron and gadolinium are useful for MRI, when used along with the antibodies of the invention. Macrocyclic chelates such as NOTA, DATA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates such as macrocyclic polyethers, which are of interest for stably binding nuclides, such as $^{223}Ra$ for RAIT are encompassed by the invention.

An immunoconjugate is a conjugate of an antibody component with a therapeutic or diagnostic agent. The diagnostic agent can comprise a radioactive or non-radioactive label, a contrast agent (such as for magnetic resonance imaging, computed tomography or ultrasound), and the radioactive label can be a gamma-, beta-, alpha-, Auger electron-, or positron-emitting isotope.

An expression vector is a DNA molecule comprising a gene that is expressed in a host cell. Typically, gene expression is placed under the control of certain regulatory elements, including constitutive or inducible promoters, tissue-specific regulatory elements and enhancers. Such a gene is said to be "operably linked to" the regulatory elements.

A recombinant host may be any prokaryotic or eukaryotic cell that contains either a cloning vector or expression vector. This term also includes those prokaryotic or eukaryotic cells, such as bacteria, yeast and mammalian cells, as well as an transgenic animal, that have been genetically engineered to contain the cloned gene(s) in the chromosome or genome of the host cell or cells of the host cells. Suitable mammalian host cells include myeloma cells, such as SP2/O cells, and NSO cells, as well as Chinese Hamster Ovary (CHO) cells, hybridoma cell lines and other mammalian host cell useful for expressing antibodies. Also particularly useful to express mAbs and other fusion proteins, is a human cell line, PER.C6 disclosed in WO 0063403 A2, which produces 2 to 200-fold more recombinant protein as compared to conventional mammalian cell lines, such as CHO, COS, Vero, Hela, BHK and SP2-cell lines. Special transgenic animals with a modified immune system are particularly useful for making fully human antibodies.

As used herein, the term antibody fusion protein is a recombinantly produced antigen-binding molecule in which two or more of the same or different single-chain antibody or antibody fragment segments with the same or different specificities are linked. Valency of the fusion protein indicates how many binding arms or sites the fusion protein has to a single antigen or epitope; i.e., monovalent, bivalent, trivalent or mutlivalent. The multivalency of the antibody fusion protein means that it can take advantage of multiple interactions in binding to an antigen, thus increasing the avidity of binding to the antigen. Specificity indicates how many antigens or epitopes an antibody fusion protein is able to bind; i.e., monospecific, bispecific, trispecific, multispecific. Using these definitions, a natural antibody, e.g., an IgG, is bivalent because it has two binding arms but is monospecific because it binds to one epitope. Monospecific, multivalent fusion proteins have more than one binding site for an epitope but only binds with one epitope, for example a diabody with two binding site reactive with the same antigen. The fusion protein may comprise a single antibody component, a multivalent or multispecific combination of different antibody components or multiple copies of the same antibody component. The fusion protein may additionally comprise an antibody or an antibody fragment and a therapeutic agent. Examples of therapeutic agents suitable for such fusion proteins include immunomodulators ("antibody-immunomodulator fusion protein") and toxins ("antibody-toxin fusion protein"). One preferred toxin comprises a ribonuclease (RNase), preferably a recombinant RNase.

A multispecific antibody is an antibody that can bind simultaneously to at least two targets that are of different structure, e.g., two different antigens, two different epitopes on the same antigen, or a hapten and/or an antigen or epitope. One specificity would be for a B-cell, T-cell, myeloid-, plasma-, and mast-cell antigen or epitope. Another specificity could be to a different antigen on the same cell type, such as CD20, CD19, CD21, CD23, CD46, CD80, HLA-DR, CD74, and CD22 on B-cells. Multispecific, multivalent antibodies are constructs that have more than one binding site, and the binding sites are of different specificity. For example, a diabody, where one binding site reacts with one antigen and the other with another antigen.

A bispecific antibody is an antibody that can bind simultaneously to two targets which are of different structure. Bispecific antibodies (bsAb) and bispecific antibody fragments (bsFab) have at least one arm that specifically binds to, for example, a B-cell, T-cell, myeloid-, plasma-, and mast-cell antigen or epitope and at least one other arm that specifically binds to a targetable conjugate that bears a therapeutic or diagnostic agent. A variety of bispecific fusion proteins can be produced using molecular engineering. In one form, the bispecific fusion protein is monovalent, consisting of, for example, a scFv with a single binding site for one antigen and a Fab fragment with a single binding site for a second antigen. In another form, the bispecific fusion protein is divalent, consisting of, for example, an IgG with a binding site for one antigen and two scFv with two binding sites for a second antigen.

Caninized or felinized antibodies are recombinant proteins in which rodent (or another species) complementarity determining regions of a monoclonal antibody have been transferred from heavy and light variable chains of rodent (or another species) immunoglobulin into a dog or cat, respectively, immunoglobulin variable domain.

Domestic animals include large animals such as horses, cattle, sheep, goats, llamas, alpacas, and pigs, as well as companion animals. In a preferred embodiment, the domestic animal is a horse.

Companion animals include animals kept as pets. These are primarily dogs and cats, although small rodents, such as guinea pigs, hamsters, rats, and ferrets, are also included, as are subhuman primates such as monkeys. In a preferred embodiment the companion animal is a dog or a cat.

Preparation of Monoclonal Antibodies including Chimeric, Humanized and Human Antibodies Monoclonal antibodies (MAbs) are a homogeneous population of antibodies to a particular antigen and the antibody comprises only one type of antigen binding site and binds to only one epitope on an antigenic determinant. Rodent monoclonal antibodies to specific antigens may be obtained by methods known to those skilled in the art. See, for example, Kohler and Milstein, Nature 256: 495 (1975), and Coligan et al. (eds.), CURRENT PROTOCOLS IN IMMUNOLOGY, VOL. 1, pages 2.5.1-2.6.7 (John Wiley & Sons 1991) [hereinafter "Coligan"]. Briefly, monoclonal antibodies can be obtained by injecting mice with a composition comprising an antigen, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992).

After the initial raising of antibodies to the immunogen, the antibodies can be sequenced and subsequently prepared by recombinant techniques. Humanization and chimerization of murine antibodies and antibody fragments are well known to those skilled in the art. For example, humanized monoclonal antibodies are produced by transferring mouse complementary determining regions from heavy and light variable chains of the mouse immunoglobulin into a human variable domain, and then, substituting human residues in the framework regions of the murine counterparts. The use of antibody components derived from humanized monoclonal antibodies obviates potential problems associated with the immunogenicity of murine constant regions.

General techniques for cloning murine immunoglobulin variable domains are described, for example, by the publication of Orlandi et al., Proc. Nat'l Acad. Sci. USA 86: 3833 (1989), which is incorporated by reference in its entirety. Techniques for constructing chimeric antibodies are well known to those of skill in the art. As an example, Leung et al., Hybridoma 13:469 (1994), describe how they produced an LL2 chimera by combining DNA sequences encoding the VK and VH domains of LL2 monoclonal antibody, an anti-CD22 antibody, with respective human kappa and IgG$_1$ constant region domains. This publication also provides the nucleotide sequences of the LL2 light and heavy chain variable regions, VK and VH, respectively. Techniques for producing humanized MAbs are described, for example, by Jones et al., Nature 321: 522 (1986), Riechmann et al., Nature 332: 323 (1988), Verhoeyen et al., Science 239: 1534 (1988), Carter et al., Proc. Nat'l Acad. Sci. USA 89: 4285 (1992), Sandhu, Crit. Rev. Biotech. 12: 437 (1992), and Singer et al., J. Immun. 150: 2844 (1993), each of which is hereby incorporated by reference.

To this end, the present invention describes chimeric, humanized and human antibodies and fragments thereof that bind the CD74 antigen and can be used for diagnostic and therapeutic methods. Humanized antibodies and antibody fragments are described in Provisional U.S. Application titled "Anti-CD20 Antibodies And Fusion Proteins Thereof And Methods Of Use", U.S. Provisional No. 60/356,132, U.S. Provisional Application No. 60/416,232 and Ser. No. 10/366, 709; hMN-14 antibodies, such as those disclosed in U.S. Pat. No. 5,874,540, which is a Class III anti-carcinoembryonic antigen antibody (anti-CEA antibody); Mu-9 antibodies, such as those described in U.S. application Ser. No. 10/116, 116; AFP antibodies, such as those described in U.S. Provisional Application No. 60/399,707; PAM4 antibodies, such as those described in Provisional U.S. Application Ser. No. 60/388,313 titled "Monoclonal Antibody cPAM4"; RS7 antibodies, such as those described in U.S. Provisional Application No. 60/360,229; and CD22 antibodies, such as those disclosed in U.S. Pat. Nos. 5,789,554 and 6,187,287 and U.S. application Ser. Nos. 09/741,843 and 09/988,013, all of which are incorporated herein by reference in their entirety.

A chimeric antibody is a recombinant protein that contains the variable domains including the CDRs derived from one species of animal, such as a rodent antibody, while the remainder of the antibody molecule; i.e., the constant domains, is derived from a human antibody. Accordingly, a chimeric monoclonal antibody can also be humanized by replacing the sequences of the murine FR in the variable domains of the chimeric mAb with one or more different human FR. Specifically, mouse CDRs are transferred from heavy and light variable chains of the mouse immunoglobulin into the corresponding variable domains of a human antibody. As simply transferring mouse CDRs into human FRs often results in a reduction or even loss of antibody affinity, additional modification might be required in order to restore the original affinity of the murine antibody. This can be accomplished by the replacement of one or more some human residues in the FR regions with their murine counterparts to obtain an antibody that possesses good binding affinity to its epitope. See, for example, Tempest et al., *Biotechnology* 9:266 (1991) and Verhoeyen et al., *Science* 239:1534 (1988). Further, the affinity of humanized, chimeric and human MAbs to a specific epitope can be increased by mutagenesis of the CDRs, so that a lower dose of antibody may be as effective as a higher dose of a lower affinity MAb prior to mutagenesis. See for example, WO 0029584A 1.

Another method for producing the antibodies of the present invention is by production in the milk of transgenic livestock. See, e.g., Colman, A., *Biochem. Soc. Symp.*, 63: 141-147, 1998; U.S. Pat. No. 5,827,690, both of which are incorporated in their entirety by reference. Two DNA constructs are prepared which contain, respectively, DNA segments encoding paired immunoglobulin heavy and light chains. The DNA segments are cloned into expression vectors which contain a promoter sequence that is preferentially expressed in mammary epithelial cells. Examples include, but are not limited to, promoters from rabbit, cow and sheep casein genes, the cow α-lactoglobulin gene, the sheep β-lactoglobulin gene and the mouse whey acid protein gene. Preferably, the inserted fragment is flanked on its 3' side by cognate genomic sequences from a mammary-specific gene. This provides a polyadenylation site and transcript-stabilizing sequences. The expression cassettes are coinjected into the pronuclei of fertilized, mammalian eggs, which are then implanted into the uterus of a recipient female and allowed to gestate. After birth, the progeny are screened for the presence of both transgenes by Southern analysis. In order for the antibody to be present, both heavy and light chain genes must be expressed concurrently in the same cell. Milk from transgenic females is analyzed for the presence and functionality of the antibody or antibody fragment using standard immunological methods known in the art. The antibody can be purified from the milk using standard methods known in the art.

A fully human antibody of the present invention, i.e., human anti-CD74 MAbs or other human antibodies, such as anti-CD22, anti-CD 19, anti-CD23, anti-CD20 or anti-CD21 MAbs for combination therapy with humanized, chimeric or human anti-CD74 antibodies, can be obtained from a transgenic non-human animal. See, e.g., Mendez et al., *Nature Genetics*, 15: 146-156 (1997); U.S. Pat. No. 5,633,425, which are incorporated in their entirety by reference. For example, a human antibody can be recovered from a transgenic mouse possessing human immunoglobulin loci. The mouse humoral immune system is humanized by inactivating the endogenous immunoglobulin genes and introducing human immunoglobulin loci. The human immunoglobulin loci are exceedingly complex and comprise a large number of discrete segments which together occupy almost 0.2% of the human genome. To ensure that transgenic mice are capable of producing adequate repertoires of antibodies, large portions of human heavy- and light-chain loci must be introduced into the mouse genome. This is accomplished in a stepwise process beginning with the formation of yeast artificial chromosomes (YACs) containing either human heavy- or light-chain immunoglobulin loci in germline configuration. Since each insert is approximately 1 Mb in size, YAC construction requires homologous recombination of overlapping fragments of the immunoglobulin loci. The two YACs, one containing the heavy-chain loci and one containing the light-chain loci, are introduced separately into mice via fusion of YAC-containing yeast spheroblasts with mouse embryonic stem cells. Embryonic stem cell clones are then microinjected into mouse blastocysts. Resulting chimeric males are screened for their ability to transmit the YAC through their germline and are bred with mice deficient in murine antibody production. Breeding the two transgenic strains, one containing the human heavy-chain loci and the other containing the human light-chain loci, creates progeny which produce human antibodies in response to immunization.

Further recent methods for producing bispecific mAbs include engineered recombinant mAbs which have additional cysteine residues so that they crosslink more strongly than the more common immunoglobulin isotypes. See, e.g., FitzGerald et al., Protein Eng. 10 (10): 1221-1225, 1997. Another approach is to engineer recombinant fusion proteins linking two or more different single-chain antibody or antibody fragment segments with the needed dual specificities. See, e.g., Coloma et al., *Nature Biotech.* 15:159-163, 1997. A variety of bispecific fusion proteins can be produced using molecular engineering. In one form, the bispecific fusion protein is monovalent, consisting of, for example, a scFv with a single binding site for one antigen and a Fab fragment with a single binding site for a second antigen. In another form, the bispecific fusion protein is divalent, consisting of, for example, an IgG with two binding sites for one antigen and two scFv with two binding sites for a second antigen.

Bispecific fusion proteins linking two or more different single-chain antibodies or antibody fragments are produced in similar manner. Recombinant methods can be used to produce a variety of fusion proteins. For example, a fusion protein comprising a Fab fragment derived from a humanized monoclonal anti-CD74 antibody and a scFv derived from a murine anti-diDTPA can be produced. A flexible linker, such as GGGS (SEQ ID NO: 15) connects the scFv to the constant region of the heavy chain of the anti-CD74 antibody. Alternatively, the scFv can be connected to the constant region of the light chain of another humanized antibody. Appropriate linker sequences necessary for the in-frame connection of the heavy chain Fd to the scFv are introduced into the Vλ and Vκ domains through PCR reactions. The DNA fragment encoding the scFv is then ligated into a staging vector containing a DNA sequence encoding the CH1 domain. The resulting scFvCH 1 construct is excised and ligated into a vector containing a DNA sequence encoding the VH region of an anti-CD74 antibody. The resulting vector can be used to transfect an appropriate host cell, such as a mammalian cell for the expression of the bispecific fusion protein.

Production of Antibody Fragments

Antibody fragments which recognize specific epitopes can be generated by known techniques. The antibody fragments are antigen binding portions of an antibody, such as F(ab')$_2$, Fab', Fab, Fv, sFv and the like. Other antibody fragments include, but are not limited to: the F(ab')$_2$ fragments which can be produced by pepsin digestion of the antibody molecule and the Fab' fragments, which can be generated by reducing disulfide bridges of the F(ab')$_2$ fragments. Alternatively, Fab' expression expression libraries can be constructed (Huse et al., 1989, *Science*, 246: 1274-1281) to allow rapid and easy identification of monoclonal Fab' fragments with the desired specificity. The present invention encompasses antibodies and antibody fragments.

A single chain Fv molecule (scFv) comprises a VL domain and a VH domain. The VL and VH domains associate to form a target binding site. These two domains are further covalently linked by a peptide linker (L). A scFv molecule is denoted as either VL-L-VH if the VL domain is the N-terminal part of the scFv molecule, or as VH-L-VL if the VH domain is the N-terminal part of the scFv molecule. Methods for making scFv molecules and designing suitable peptide linkers are described in U.S. Pat. No. 4,704,692, U.S. Pat. No. 4,946,778, R. Raag and M. Whitlow, "*Single Chain Fvs.*" FASEB Vol 9:73-80 (1995) and R. E. Bird and B. W. Walker, "*Single Chain Antibody Variable Regions,*" TIBTECH, Vol 9: 132-137 (1991). These references are incorporated herein by reference.

An antibody fragment can be prepared by proteolytic hydrolysis of the full-length antibody or by expression in *E. coli* or another host of the DNA coding for the fragment. An antibody fragment can be obtained by pepsin or papain digestion of full length antibodies by conventional methods. For example, an antibody fragment can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using papain produces two monovalent Fab fragments and an Fc fragment directly. These methods are described, for example, by Goldenberg, U.S. Pat. Nos. 4,036,945 and 4,331,647 and references contained therein, which patents are incorporated herein in their entireties by reference. Also, see Nisonoff et al., *Arch Biochem. Biophys.* 89:230 (1960); Porter, *Biochem. J.* 73: 119 (1959), Edelman et al., in METHODS IN ENZYMOLOGY VOL. 1, page 422 (Academic Press 1967), and Coligan at pages 2.8.1-2.8.10 and 2.10.-2.10.4.

Another form of an antibody fragment is a peptide coding for a single complementarity-determining region (CDR). A CDR is a segment of the variable region of an antibody that is complementary in structure to the epitope to which the antibody binds and is more variable than the rest of the variable region. Accordingly, a CDR is sometimes referred to as hypervariable region. A variable region comprises three CDRs. CDR peptides can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: A Companion to Methods in Enzymology* 2: 106 (1991); Courtenay-Luck, "Genetic Manipulation of Monoclonal Antibodies," in MONOCLONAL ANTIBODIES: PRODUCTION, ENGINEERING AND CLINICAL APPLICATION, Ritter et al. (eds.), pages 166-179 (Cambridge University Press 1995); and Ward et al., "Genetic Manipulation and Expression of Antibodies," in MONOCLONAL ANTIBODIES: PRINCIPLES AND APPLICATIONS, Birch et al., (eds.), pages 137-185 (Wiley-Liss, Inc. 1995).

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

Anti-CD74 Antibodies

The anti-CD74 mAbs of the present invention contain specific murine CDRs that have specificity for the CD74 antigen. The anti-CD74 mAbs of the present invention are humanized, chimeric or human mAbs and they contain the amino acids of the CDRs of a murine anti-CD74 mAb, the murine LL1 mAb. The humanized anti-CD74 monoclonal antibody (mAb) or fragment thereof comprise CDRs of a light chain variable region of a murine anti-CD74 mAb, that comprises CDR1 comprising an amino acid sequence RSSQSLVHRNGNTYLH (SEQ ID NO:16), CDR2 comprising an amino acid sequence TVSNRFS (SEQ ID NO:17), and CDR3 comprising an amino acid sequence SQSSIHVPPT (SEQ ID NO:18). Further, the humanized anti-CD74 monoclonal antibody or fragment thereof comprises the heavy chain variable region of said humanized mAb that comprises CDRs of a heavy chain variable region of a murine anti-CD74 mAb, that comprises CDR1 comprising an amino acid sequence NYGVN (SEQ ID NO:19), CDR2 comprising an amino acid sequence WINPNTGEPTFDDDFKG (SEQ ID NO:20), and CDR3 comprising an amino acid sequence SRGKNEAWFAY (SEQ ID NO:21). Further, the humanized mAb retains substantially the specificity for the CD74, i.e., the MHC class-II invariant chain, Ii, present on the surface of cells, such as B-lymphocytes, monocyte and histiocytes, as well as B-cell lymphoma and leukemia, as well as myeloma cells resulting in the rapid internalization and catabolization of these mAbs, fragments thereof or mAb conjugates.

In one embodiment, a CD74 antibodies of the present invention is a humanized anti-CD74 monoclonal antibody (mAb) or fragment thereof comprising light and heavy chain variable regions comprising complementarity-determining regions (CDRs) of murine anti-CD74 (mLL1) and the framework (FR) regions of a human antibody, wherein the light chain variable region of the humanized mAb comprises CDRs of a light chain variable region of a murine anti-CD74 mAb, that comprises CDR1 comprising an amino acid sequence RSSQSLVHRNGNTYLH (SEQ ID NO:16), CDR2 comprising an amino acid sequence TVSNRFS (SE ID NO: 17), and CDR3 comprising an amino acid sequence SQSSHVPPT (SEQ ID NO:18), and wherein the heavy chain variable region of the humanized mAb comprises CDRs of a heavy chain variable region of a murine anti-CD74 mAb, that comprises CDR1 comprising an amino acid sequence NYGVN (SEQ ID NO:19), CDR2 comprising an amino acid sequence WINPNTGEPTFDDDFKG (SEQ ID NO:20), and CDR3 comprising an amino acid sequence SRGKNEAWFAY (SEQ ID NO:21). The murine CDRs of the heavy and light chain variable regions are shown in FIGS. 1A and 1B, respectively. The human FRs of the light and heavy chain variable regions may be modified to maintain specificity to CD74 by substituting at least one amino acid substituted from the corresponding FRs of the murine mAb. More specifically, one or more specific amino acids from the murine mAb identified by amino acid residue 2, 3, 4, 46, 87 and 100 of the murine light chain variable region of the cLL1Vk sequence of FIG. 3B, and amino acid residues 5, 37, 38, 46, 68, 91 and 93 of the murine heavy chain variable region of the cLL1VH sequence of FIG. 3A may be maintained in the human FRs of the humanized anti-CD74 to maintain specificity.

In a preferred embodiment, the humanized anti-CD74 mAb, the humanized LL1 (hLL1) or fragment thereof containing a heavy chain variable region of FIG. 4A and a light chain variable region of FIG. 4B is used in the methods disclosed in the present invention. More specifically, the humanized anti-CD74 mAb or fragment thereof contains a light and heavy chain constant region of a human antibody or a portion thereof. Additionally, the humanized anti-CD74 mAb or fragment thereof of anyone of the humanized anti-CD74 mAbs or fragments thereof, described herein, can be a humanized IgG1.

Although humanized anti-CD74 mAbs are preferred, chimeric anti-CD74 (cCD74) mAbs or fragments thereof also are encompassed by the present invention. In one embodiment, the chimeric anti-CD74 monoclonal antibody, (mAb) or fragment thereof comprises a light chain variable region of a murine anti-CD74 mAb, that comprises CDR1 comprising an amino acid sequence RSSQSLVHRNGNTYLH (SEQ ID NO:16), CDR2 comprising an amino acid sequence TVSNRFS (SEQ ID NO:17), and CDR3 comprising an amino acid sequence SQSSHVPPT (SEQ ID NO:18). In a further embodiment, the chimeric anti-CD74 monoclonal antibody or fragment thereof comprises a heavy chain variable region of a murine anti-CD74 mAb, that comprises CDR1 comprising an amino acid sequence NYGVN (SEQ ID NO:19), CDR2 comprising an amino acid sequence WINPNTGEPTFDDDFKG (SEQ ID NO:20), and CDR3 comprising an amino acid sequence SRGKNEAWFAY (SEQ ID NO:21). In a further embodiment the chimeric anti-CD74 mAb comprises light and heavy chain variable regions comprising complementarity-determining regions (CDRs) of a murine anti-CD74 mAb and the framework (FR) regions of a murine anti-CD74 mAb and the light and heavy chain constant regions of a human antibody, wherein the light chain variable region of the chimeric mAb comprises CDRs of a light chain variable region of a murine antiCD74 mAb, that comprises CDR1 comprising an amino acid sequence RSSQSLVHRNGNTYLH (SEQ ID NO:16), CDR2 comprising an amino acid sequence TVSNRFS (SEQ ID NO:17), and CDR3 comprising an amino acid sequence SQSSHVPPT (SEQ ID NO:18), and wherein the heavy chain variable region of said chimeric mAb comprises CDRs of a heavy chain variable region of a murine anti-CD74 mAb, that comprises CDR1 comprising an amino acid sequence NYGVN (SEQ ID NO:19), CDR2 comprising an amino acid sequence WINPNTGEPTFDDDFKG (SEQ ID NO:20), and CDR3 comprising an amino acid sequence SRGKNEAWFAY (SEQ ID NO:21). The preferred chimeric anti-CD74 mAb or fragment thereof comprises a heavy chain variable region of FIG. 2A and a light chain variable region of FIG. 2B.

Also encompassed within the present invention is a human anti-CD74 monoclonal antibody (mAb) or fragment thereof comprising a light chain variable region of the human anti-CD74 mAb that comprises CDR1 comprising an amino acid sequence RSSQSLVHRNGNTYLH (SEQ ID NO:16), CDR2 comprising an amino acid sequence TVSNRFS (SEQ ID NO:17), and CDR3 comprising an amino acid sequence SQSSHVPPT (SEQ ID NO:18). Further, encompasses is a human anti-CD74 monoclonal antibody (mAb) or fragment thereof comprising a heavy chain variable region of said human mAb that comprises CDRs of a heavy chain variable region of a murine anti-CD74 mAb, that comprises CDR1 comprising an amino acid sequence NYGVN (SEQ ID NO:19), CDR2 comprising an amino acid sequence WINPNTGEPTFDDDFKG (SEQ ID NO:20), and CDR3 comprising an amino acid sequence SRGKNEAWFAY (SEQ ID NO:21). More preferably, the present invention discloses a human anti-CD74 (huCD74) monoclonal antibody (mAb) or fragment thereof comprising the light and heavy chain variable and constant regions of a human antibody, wherein the huCD74 CDRs of the light chain variable region of the human anti-CD74 mAb comprises CDR1 comprising an amino acid sequence RSSQSLVHRNGNTYLH (SEQ ID NO: 16), CDR2 comprising an amino acid sequence TVSNRFS (SEQ ID NO: 17), and CDR3 comprising an amino acid sequence SQSSHVPPT (SEQ ID NO: 18), and wherein the heavy chain variable region of the human mAb comprises CDRs of a heavy chain variable region of a murine anti-CD74 mAb, that comprises CDR1 comprising an amino acid sequence NYGVN (SEQ ID NO: 19), CDR2 comprising an amino acid sequence WINPNTGEPTFDDDFKG (SEQ ID NO: 20), and CDR3 comprising an amino acid sequence SRGKNEAWFAY (SEQ ID NO: 21).

Each of the human, chimeric or humanized anti-CD74 mAb of the present invention is preferably an IgG1, where the constant regions are preferably a human IgG1, but the IgG1 may be referred to as a human IgG1, a chimeric IgG1 or a humanized IgG1, respectively. In particular, the humanized CD74 mAb, hLL1, has constant domains and the hinge region from a human IgG1. Preferably, both the chimeric and the human LL1 mAb has the same constant domain and hinge region. However, modifications can be made so that the constant regions of the IgG1 are replaced with with human constant regions of human IgG2a, IgG3 or IgG4.

The present invention also is directed to a murine anti-CD74 monoclonal antibody or fragment thereof, comprising CDRs of a light chain variable region of a murine anti-CD74 mAb, that comprises CDR1 comprising an amino acid sequence RSSQSLVHRNGNTYLH (SEQ ID NO:16), CDR2 comprising an amino acid sequence TVSNRFS (SEQ ID NO:17), and CDR3 comprising an amino acid sequence SQSSHVPPT (SEQ ID NO:18). Further, the murine antiCD74 monoclonal antibody or fragment thereof, comprising CDRs of a heavy chain variable region of a murine anti-CD74 mAb, that comprises CDR1 comprising an amino acid sequence NYGVN (SEQ ID NO:19), CDR2 comprising an amino acid sequence WINPNTGEPTFDDDFKG (SEQ ID NO:20), and CDR3 comprising an amino acid sequence SRGKNEAWFAY (SEQ ID NO:21). More preferably, the murine anti-CD74 monoclonal antibody or fragment thereof comprising complementarity-determining regions (CDRs) of murine anti-CD74 (mLL1) and the framework (FR) regions of a murine anti-CD74 antibody, wherein the light chain variable region of said murine mAb comprises CDR1 comprising an amino acid sequence RSSQSLVHRNGNTYLH (SEQ ID NO:16), CDR2 comprising an amino acid sequence TVSNRFS (SEQ ID NO:17), and CDR3 comprising an amino acid sequence SQSSHVPPT (SEQ ID NO:18), and wherein the heavy chain variable region of said murine mAb comprises CDR1 comprising an amino acid sequence NYGVN (SEQ ID NO:19), CDR2 comprising an amino acid sequence WINPNTGEPTFDDDFKG (SEQ ID NO:20), and CDR3 comprising an amino acid sequence SRGKNEAWFAY (SEQ ID NO:21).

Each of the human, chimeric, humanized or murine anti-CD74 mAbs or fragment thereof of the present invention possess at least one of the following properties: it binds specifically and is reactive with the antigen, CD74, its binding to CD74 is blocked by an antibody or fragment thereof specific for or reactive with CD74; it is internalized by Raji lymphoma cells in culture; and it induces apoptosis of Raji cells in cell culture when cross-linked with goat antisera reactive with the Fc of a murine IgG1 mAb.

The fragments of the human, chimeric or humanized anti-CD74 mAb may be a fragment, such is F(ab')₂, Fab, scFv, Fv, or a fusion construct utilizing part or all the light and heavy chains of the F(ab')2, Fab, scFv, or Fv. It is important that the fragment binds to CD74.

Multispecific and Multivalent Antibodies

The anti-CD74 antibodies, as well as other antibodies with different specificities for use in combination therapy, described herein, can also be made as multispecific antibodies (comprising at least one binding site to a CD74 epitope or antigen and at least one binding site to another epitope on CD74 or another antigen) and multivalent antibodies (comprising multiple binding sites to the same epitope or antigen), or the antibodies can be both multivalent and multispecific.

A preferred antibody fusion protein of the present invention contains four or more Fvs, or Fab's of the humanized, chimeric, human or murine anti-CD74 mAbs or fragments thereof described herein. Additionally, another preferred antibody fusion protein contains one or more Fvs, or Fab's of the mAbs or fragments thereof of the humanized, chimeric, human or murine anti-CD74 mAbs or fragments thereof described herein, and one or more Fvs or Fab's from antibodies specific for another antigen that is specific for a tumor cell marker that is not a CD74 antigen, that is expressed by the CD74-expressing cells, such as, for example, a tumor marker selected from a B-cell lineage antigen, such as CD19, CD20, or CD22 for the treatment of B-cell malignancies; as well as other CD74 positive cells causing other types of malignancies, such as S100 in melanoma, etc. Further, the tumor cell marker may be a non-B-cell lineage antigen selected from the group consisting of HLA-DR, CD30, CD33, CD52 MUC1 and TAC.

The present invention also provides a bispecific or multispecific antibody, wherein the anti-CD74 mAbs or fragments thereof or antibody fusion proteins thereof of the present invention are linked to an antibody or antibody fragment specific for a cancer marker substance, an epitope on the surface of a infectious disease organism, or a noxious substance in the blood or other body fluids. The bispecific and multispecific antibodies of the present invention are particularly useful in the method of inducing clearance of a variety of noxious substances, where the bispecific antibody has at least one specificity for a noxious substance, such as a pathogenic organism, and at least one specificity for CD74, the HLA class-II invariant chain (Ii), as described in detail in U.S. Ser. No. 09/314,135, filed on May 19, 1999, entitled "Therapeutic Using a Bispecific Antibody," which is herein incorporated in its entirety by reference.

The present invention further provides a bispecific antibody or antibody fragment having at least a binding region that specifically binds a targeted cell marker and at least one other binding region that specifically binds a targetable conjugate. The targetable conjugate comprises a carrier portion which comprises or bears at least one epitope recognized by at least one binding region of the bispecific antibody or antibody fragment.

A variety of recombinant methods can be used to produce bispecific antibodies and antibody fragments as described above.

An anti-CD74 multivalent antibody is also contemplated in the present invention. This multivalent target binding protein is constructed by association of a first and a second polypeptide. The first polypeptide comprises a first single chain Fv molecule covalently linked to a first immunoglobulin-like domain that preferably is an immunoglobulin light chain variable region domain. The second polypeptide comprises a second single chain Fv molecule covalently linked to a second immunoglobulin-like domain that preferably is an immunoglobulin heavy chain variable region domain. Each of the first and second single chain Fv molecules forms a target binding site, and the first and second immunoglobulin-like domains associate to form a third target binding site.

A single chain Fv molecule with the VL-L-VH configuration, wherein L is a linker, may associate with another single chain Fv molecule with the VH-L-VL configuration to form a bivalent dimer. In this case, the VL domain of the first scFv and the VH domain of the second scFv molecule associate to form one target binding site, while the VH domain of the first scFv and the VL domain of the second scFv associate to form the other target binding site.

Another embodiment of the present invention is a CD74 bispecific, trivalent targeting protein comprising two heterologous polypeptide chains associated non-covalently to form three binding sites, two of which have affinity for one target and a third which has affinity for a hapten that can be made and attached to a carrier for a diagnostic and/or therapeutic agent. Preferably, the binding protein has two CD20 binding sites and one CD22 binding site. The bispecific, trivalent targeting agents have two different scFvs, one scFv contains two $V_H$ domains from one antibody connected by a short linker to the VL domain of another antibody and the second scFv contains two VL domains from the first antibody connected by a short linker to the VH domain of the other antibody. The methods for generating multivalent, multispecific agents from VH and VL domains provide that individual chains synthesized from a DNA plasmid in a host organism are composed entirely of VH domains (the VH-chain) or entirely of VL domains (the VL-chain) in such a way that any agent of multivalency and multispecificity can be produced by non-covalent association of one VH-chain with one VL-chain. For example, forming a trivalent, trispecific agent, the VH-chain will consist of the amino acid sequences of three $V_H$ domains, each from an antibody of different specificity, joined by peptide linkers of variable lengths, and the VL-chain will consist of complementary VL domains, joined by peptide linkers similar to those used for the VH-chain. Since the VH and VL domains of antibodies associate in an anti-parallel fashion, the preferred method in this invention has the VL domains in the VL-chain arranged in the reverse order of the VH domains in the VH-chain.

Diabodies, Triabodies and Tetrabodies

The anti-CD74 antibodies of the present invention can also be used to prepare functional bispecific single-chain antibodies (bscAb), also called diabodies, and can be produced in mammalian cells using recombinant methods. See, e.g., Mack et al., *Proc. Natl. Acad. Sci.*, 92: 7021-7025, 1995, incorporated. For example, bscAb are produced by joining two single-chain Fv fragments via a glycine-serine linker using recombinant methods. The V light-chain (VL) and V heavy-chain (VH) domains of two antibodies of interest are isolated using standard PCR methods. The VL and VH cDNA's obtained from each hybridoma are then joined to form a single-chain fragment in a two-step fusion PCR. The first PCR step introduces the $(Gly_4-Ser_1)_3$ linker (SEQ ID NO:22), and the second step joins the VL and VH amplicons. Each single chain molecule is then cloned into a bacterial expression vector. Following amplification, one of the single-chain molecules is excised and sub-cloned into the other vector, containing the second single-chain molecule of interest. The resulting bscAb fragment is subcloned into an eukaryotic expression vector. Functional protein expression can be obtained by transfecting the vector into Chinese Hamster Ovary cells. Bispecific fusion proteins are prepared in a similar manner. Bispecific single-chain antibodies and bispecific fusion proteins are included within the scope of the present invention.

For example, a humanized, chimeric or human anti-CD74 monoclonal antibody can be used to produce antigen specific diabodies, triabodies, and tetrabodies. The monospecific diabodies, triabodies, and tetrabodies bind selectively to targeted antigens and as the number of binding sites on the molecule increases, the affinity for the target cell increases and a longer residence time is observed at the desired location. For diabodies, the two chains comprising the VH polypeptide of the humanized CD74 mAb connected to the VK polypeptide of the humanized CD74 mAb by a five amino acid residue linker are utilized. Each chain forms one half of the humanized CD74 diabody. In the case of triabodies, the three chains comprising $V_H$ polypeptide of the humanized CD74 MAb connected to the VK polypeptide of the humanized CD74 MAb by no linker are utilized. Each chain forms one third of the hCD74 triabody.

The ultimate use of the bispecific diabodies described herein is for pretargeting CD74 positive tumors for subsequent specific delivery of diagnostic or therapeutic agents. These diabodies bind selectively to targeted antigens allowing for increased affinity and a longer residence time at the desired location. Moreover, non-antigen bound diabodies are cleared from the body quickly and exposure of normal tissues is minimized. The diagnostic and therapeutic agents can include isotopes, drugs, toxins, cytokines, hormones, enzymes, oligonucleotides, growth factors, conjugates, radionuclides, and metals. For example, gadolinium metal is used for magnetic resonance imaging (MRI). Examples of radionuclides are $^{225}$Ac, $^{18}$F, $^{68}$Ga, $^{67}$Ga, $^{90}$Y, $^{86}$Y, $^{111}$In, $^{131}$I, $^{125}$I, $^{123}$I, $^{99m}$Tc, $^{94m}$Tc, $^{186}$Re, $^{188}$Re, $^{177}$Lu, $^{62}$Cu, $^{64}$Cu, $^{67}$Cu, $^{212}$Bi, $^{213}$Bi, $^{32}$P, $^{11}$C, $^{13}$N, $^{15}$O, $^{76}$Br, and $^{211}$At. Other radionuclides are also available as diagnostic and therapeutic agents, especially those in the energy range of 60 to 4,000 keV for diagnostic agents and in the energy range of 60-700 for the therapeutic agents.

More recently, a tetravalent tandem diabody (termed tandab) with dual specificity has also been reported (Cochlovius et al., Cancer Research (2000) 60: 4336-4341). The bispecific tandab is a dimer of two identical polypeptides, each containing four variable domains of two different antibodies ($V_{H1}, V_{L1}, V_{H2}, V_{L2}$) linked in an orientation to facilitate the formation of two potential binding sites for each of the two different specificities upon self-association.

Conjugated Multivalent and Multispecific anti-CD74 Antibodies

In another embodiment of the instant invention is a conjugated multivalent anti-CD74 antibody. Additional amino acid residues may be added to either the N- or C-terminus of the first or the second polypeptide. The additional amino acid residues may comprise a peptide tag, a signal peptide, a cytokine, an enzyme (for example, a pro-drug activating enzyme), a hormone, a peptide toxin, such as pseudomonas extoxin, a peptide drug, a cytotoxic protein or other functional proteins. As used herein, a functional protein is a protein that has a biological function.

In one embodiment, drugs, toxins, radioactive compounds, enzymes, hormones, cytotoxic proteins, chelates, cytokines and other functional agents may be conjugated to the multivalent target binding protein, preferably through covalent attachments to the side chains of the amino acid residues of the multivalent target binding protein, for example amine, carboxyl, phenyl, thiol or hydroxyl groups. Various conventional linkers may be used for this purpose, for example, diisocyanates, diisothiocyanates, bis(hydroxysuccinimide) esters, carbodiimides, maleimide-hydroxysuccinimide esters, glutaraldehyde and the like. Conjugation of agents to the multivalent protein preferably does not significantly affect the protein's binding specificity or affinity to its target. As used herein, a functional agent is an agent which has a biological function. A preferred functional agent is a cytotoxic agent.

In still other embodiments, bispecific antibody-directed delivery of therapeutics or prodrug polymers to in vivo targets can be combined with bispecific antibody delivery of radionuclides, such that combination chemotherapy and radioimmunotherapy is achieved. Each therapy can be conjugated to the targetable conjugate and administered simultaneously, or the nuclide can be given as part of a first targetable conjugate and the drug given in a later step as part of a second targetable conjugate.

In another embodiment, cytotoxic agents may be conjugated to a polymeric carrier, and the polymeric carrier may subsequently be conjugated to the multivalent target binding protein. For this method, see Ryser et al., *Proc. Natl. Acad. Sci. USA*, 75:3867-3870, 1978, U.S. Pat. No. 4,699,784 and U.S. Pat. No. 4,046,722, which are incorporated herein by reference. Conjugation preferably does not significantly affect the binding specificity or affinity of the multivalent binding protein.

Humanized, Chimeric and Human Antibodies Use for Treatment and Diagnosis

Humanized, chimeric and human monoclonal antibodies, i.e., anti-CD74 mAbs and other MAbs described herein, in accordance with this invention are suitable for use in therapeutic methods and diagnostic methods. Accordingly, the present invention contemplates the administration of the humanized, chimeric and human antibodies of the present invention alone as a naked antibody or administered as a multimodal therapy, temporally according to a dosing regimen, but not conjugated to, a therapeutic agent. An immunoconjugate is a conjugate comprising an antibody component comprising at least one mAb or fragment thereof or antibody fusion protein thereof of the humanized, chimeric or human CD74 mAbs described in the present invention that binds to CD74, which is linked to a diagnostic or therapeutic agent.

The efficacy of the naked anti-CD74 mAbs can be enhanced by supplementing naked antibodies with one or more other naked antibodies, i.e., mAbs to specific antigens, such as CD4, CD5, CD8, CD14, CD15, CD19, CD21, CD22, CD23, CD25, CD30, CD33, CD37, CD38, CD40, CD40L, CD46, CD52, CD54, CD8O, CD126, B7, MUC1, 1a, tenascin, HM1.24, or HLA-DR, preferably mature HLA-DR dimer, with one or more immunoconjugates of anti-CD74, or antibodies to these recited antigens, conjugated with therapeutic agents, including drugs, toxins, immunomodulators, hormones, enzymes, therapeutic radionuclides, etc., with one or more therapeutic agents, including drugs, toxins, immunomodulators, hormones, enzymes, therapeutic radionuclides, etc., administered concurrently or sequentially or according to a prescribed dosing regimen, with the mAbs. Preferred B-cell associated antigens include those equivalent to human CD19, CD20, CD21, CD22, CD23, CD46, CD52, CD74, CD8O, and CD5 antigens. Preferred T-cell antigens include those equivalent to human CD4, CD8 and CD25 (the IL-2 receptor) antigens. An equivalent to HLA-DR antigen can be used in treatment of both B-cell and T-cell disorders. Particularly preferred B-cell antigens are those equivalent to human CD19, CD22, CD21, CD23, CD74, CD8O, and HLA-DR antigens. Particularly preferred T-cell antigens are those equivalent to human CD4, CD8 and CD25 antigens. CD46 is an antigen on the surface of cancer cells that block complement-dependent lysis (CDC). Preferred malignant melanoma associated antigens are those equivalent to MART-1, TRP-1, TRP-2 and gp100. Further, preferred multiple myeloma-associated antigens are those equivalent to MUC1 and CD38.

Further, the present invention contemplates the administration of an immunoconjugate for diagnostic and therapeutic uses in B cell lymphomas and other disease or disorders. An immunoconjugate, as described herein, is a molecule comprising an antibody component and a therapeutic or diagnostic agent, including a peptide that may bear the diagnostic or therapeutic agent. An immunoconjugate retains the immunoreactivity of the antibody component, i.e., the antibody moiety has about the same or slightly reduced ability to bind the cognate antigen after conjugation as before conjugation.

A wide variety of diagnostic and therapeutic reagents can be advantageously conjugated to the antibodies of the invention. The therapeutic agents recited here are those agents that also are useful for administration separately with the naked antibody as described above. Therapeutic agents include, for example, chemotherapeutic drugs such as vinca alkaloids, anthracyclines, epidophyllotoxins, taxanes, antimetabolites, alkylating agents, antibiotics, COX-2 inhibitors, antimitotics, antiangiogenic and apoptotoic agents, particularly doxorubicin, methotrexate, taxol, CPT-11, camptothecans, and others from these and other classes of anticancer agents, and the like. Other useful cancer chemotherapeutic drugs for the preparation of immunoconjugates and antibody fusion proteins include nitrogen mustards, alkyl sulfonates, nitrosoureas, triazenes, folic acid analogs, COX-2 inhibitors, pyrimidine analogs, purine analogs, platinum coordination complexes, hormones, and the like. Suitable chemotherapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications. Other suitable chemotherapeutic agents, such as experimental drugs, are known to those of skill in the art.

Additionally, a chelator such as DTPA, DOTA, TETA, or NOTA or a suitable peptide, to which a detectable label, such as a fluorescent molecule, or cytotoxic agent, such as a heavy metal or radionuclide, can be conjugated. For example, a therapeutically useful immunoconjugate can be obtained by conjugating a photoactive agent or dye to an antibody composite. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy (Jori et al. (eds.), PHOTODYNAMIC THERAPY OF TUMORS AND OTHER DISEASES (Libreria Progetto 1985); van den Bergh, Chem. Britain 22:430 (1986)). Moreover, monoclonal antibodies have been coupled with photoactivated dyes for achieving phototherapy. Mew et al., J. Immunol. 130:1473 (1983); idem., Cancer Res. 45:4380 (1985); Oseroff et. al., Proc. Natl. Acad. Sci. USA 83:8744 (1986); idem., Photochem. Photobiol. 46:83 (1987); Hasan et al., Prog. Clin. Biol. Res. 288:471 (1989); Tatsuta et al., Lasers Surg. Med. 9:422 (1989); Pelegrin et al., Cancer 67:2529 (1991). However, these earlier studies did not include use of endoscopic therapy applications, especially with the use of antibody fragments or subfragments. Thus, the present invention contemplates the therapeutic use of immunoconjugates comprising photoactive agents or dyes.

Also contemplated by the present invention is the use of radioactive and non-radioactive agents as diagnostic agents. A suitable non-radioactive diagnostic agent is a contrast agent suitable for magnetic resonance imaging, computed tomography or ultrasound. Magnetic imaging agents include, for example, non-radioactive metals, such as manganese, iron and gadolinium, complexed with metal-chelate combinations that include 2-benzyl-DTPA and its monomethyl and cyclohexyl analogs, when used along with the antibodies of the invention. See U.S. Ser. No. 09/921,290 filed on Oct. 10, 2001, which is incorporated in its entirety by reference.

Furthermore, a radiolabeled antibody or immunoconjugate may comprise a γ-emitting radioisotope or a positron-emitter useful for diagnostic imaging. Suitable radioisotopes, particularly in the energy range of 60 to 4,000 keV, include $^{131}$I, $^{123}$I, $^{124}$I, $^{86}$Y, $^{62}$Cu, $^{64}$Cu, $^{111}$In, $^{67}$Ga, $^{68}$Ga, $^{99m}$Tc, $^{18}$F, $^{11}$C, $^{13}$N, $^{15}$O, $^{75}$Br, and the like. See, for example, U.S. Patent Application entitled "Labeling Targeting Agents with Gallium-68"—Inventors G. L. Griffiths and W. J. McBride, (U.S. Provisional Application No. 60/342,104), which discloses positron emitters, such as $^{18}$F, $^{68}$Ga, $^{94m}$Tc. and the like, for imaging purposes and which is incorporated in its entirety by reference.

A toxin, such as *Pseudomonas* exotoxin, may also be complexed to or form the therapeutic agent portion of an antibody fusion protein of an anti-CD74 antibody of the present invention. Other toxins suitably employed in the preparation of such conjugates or other fusion proteins, include ricin, abrin, ribonuclease (RNase), DNase I, *Staphylococcal* enterotoxin-A, pokeweed antiviral protein, gelonin, diphtherin toxin, *Pseudomonas* exotoxin, and *Pseudomonas* endotoxin. See, for example, Pastan et al., Cell 47:641 (1986), and Goldenberg, C A—A Cancer Journal for Clinicians 44:43 (1994). Additional toxins suitable for use in the present invention are known to those of skill in the art and are disclosed in U.S. Pat. No. 6,077,499, which is incorporated in its entirety by reference.

An immunomodulator, such as a cytokine may also be conjugated to, or form the therapeutic agent portion of an antibody fusion protein or be administered with the humanized anti-CD20 antibodies of the present invention. Suitable cytokines for the present invention include, but are not limited to, interferons and interleukins, as described below.

Also contemplated by the present invention is a vaccine comprising the humanized, chimeric or human CD74 mAabs or fragments thereof or an antibody fusion protein thereof covalently linked to Class-I or Class-II MHC antigenic peptides forming an antibody conjugate, wherein the vaccine is used to treat patients with cancer or infectious disease. When the antibody conjugate is internalized by the cell containing the CD74 marker, the Class-I or Class-II antigenic peptides are released by protolytic digestion from a larger peptide or protein linked to the Mab or fragment thereof, by a antigen presenting cell, such as a dendritic cell. This antibody conjugate is prepared by fusing cDNA coding for the mAb or fragment thereof with cDNA coding for the antigenic peptide or protein, and expressing the fusion protein in a bacteria, yeast, or mammalian cell. Antibody conjugates containing the humanized, chimeric or human CD74 MAbs or fragments thereof or antibody fusion proteins of the present invention are particularly useful in a method of treatment described in pending U.S. Ser. No. 08/577,106, filed on Dec. 22, 1995, entitled "Use of Immunoconjugates to Enhance the Efficacy of Multi-Stage Cascade Boosting Vaccines," which is herein incorporated in its entirety by reference. The humanized anti-CD74 MAb of the present invention is particularly useful in place of the murine LL1 in Example 5.

Preparation of Immunoconjugates

Any of the antibodies or antibody fusion proteins of the present invention can be conjugated with one or more therapeutic or diagnostic agents. Generally, one therapeutic or diagnostic agent is attached to each antibody or antibody fragment but more than one therapeutic agent or diagnostic agent can be attached to the same antibody or antibody fragment. The antibody fusion proteins of the present invention comprise two or more antibodies or fragments thereof and each of the antibodies that comprises this fusion protein can contain a therapeutic agent or diagnostic agent. Additionally, one or more of the antibodies of the antibody fusion protein can have more than one therapeutic of diagnostic agent attached. Further, the therapeutic agents do not need to be the same but can be different therapeutic agents. For example, one can attach a drug and a radioisotope to the same fusion protein. Particularly, an IgG can be radiolabeled with $^{131}$I and attached to a drug. The $^{131}$I can be incorporated into the tyrosine of the IgG and the drug attached to the epsilon amino group of the IgG lysines. Both therapeutic and diagnostic agents also can be attached to reduced SH groups and to the carbohydrate side chains.

Bispecific antibodies of the present invention are useful in pretargeting methods and provide a preferred way to deliver two therapeutic agents or two diagnostic agents to a subject. U.S. Ser. No. 09/382,186 discloses a method of pretargeting using a bispecific antibody, in which the bispecific antibody is labeled with $^{125}$I and delivered to a subject, followed by a divalent peptide labeled with $^{99m}$Tc. The delivery results in excellent tumor/normal tissue ratios for $^{125}$I and $^{99m}$Tc, thus showing the utility of two diagnostic radioisotopes. Any combination of known therapeutic agents or diagnostic agents can be used to label the antibodies and antibody fusion proteins. The binding specificity of the antibody component of the mAb conjugate, the efficacy of the therapeutic agent or diagnostic agent and the effector activity of the Fc portion of the antibody can be determined by standard testing of the conjugates.

A therapeutic or diagnostic agent can be attached at the hinge region of a reduced antibody component via disulfide bond formation. As an alternative, such peptides can be attached to the antibody component using a heterobifunctional cross-linker, such as N-succinyl 3-(2-pyridyldithio) proprionate (SPDP). Yu et al., *Int. J. Cancer* 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995). Alternatively, the therapeutic or diagnostic agent can be conjugated via a carbohydrate moiety in the Fc region of the antibody. The carbohydrate group can be used to increase the loading of the same peptide that is bound to a thiol group, or the carbohydrate moiety can be used to bind a different peptide.

Methods for conjugating peptides to antibody components via an antibody carbohydrate moiety are well-known to those of skill in the art. See, for example, Shih et al., *Int. J. Cancer* 41: 832 (1988); Shih et al., *Int. J. Cancer* 46: 1101 (1990); and Shih et al., U.S. Pat. No. 5,057,313, all of which are incorporated in their entirety by reference. The general method involves reacting an antibody component having an oxidized carbohydrate portion with a carrier polymer that has at least one free amine function and that is loaded with a plurality of peptide. This reaction results in an initial Schiff base (imine) linkage, which can be stabilized by reduction to a secondary amine to form the final conjugate.

The Fc region is absent if the antibody used as the antibody component of the immunoconjugate is an antibody fragment. However, it is possible to introduce a carbohydrate moiety into the light chain variable region of a full-length antibody or antibody fragment. See, for example, Leung et al., *J. Immunol.* 154: 5919 (1995); Hansen et al., U.S. Pat. No. 5,443,953 (1995), Leung et al., U.S. Pat. No. 6,254,868, all of which are incorporated in their entirety by reference. The engineered carbohydrate moiety is used to attach the therapeutic or diagnostic agent.

Pharmaceutically Acceptable Excipients

The humanized, chimeric and human anti-CD74 mAbs to be delivered to a subject can consist of the mAb alone, immunoconjugate, fusion protein, or can comprise one or more pharmaceutically suitable excipients, one or more additional ingredients, or some combination of these.

The immunoconjugate or naked antibody of the present invention can be formulated according to known methods to prepare pharmaceutically useful compositions, whereby the immunoconjugate or naked antibody are combined in a mixture with a pharmaceutically suitable excipient. Sterile phosphate-buffered saline is one example of a pharmaceutically suitable excipient. Other suitable excipients are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The immunoconjugate or naked antibody of the present invention can be formulated for intravenous administration via, for example, bolus injection or continuous infusion. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Additional pharmaceutical methods may be employed to control the duration of action of the therapeutic or diagnostic conjugate or naked antibody. Control release preparations can be prepared through the use of polymers to complex or absorb the immunoconjugate or naked antibody. For example, biocompatible polymers include matrices of poly(ethylene-co-vinyl acetate) and matrices of a polyanhydride copolymer of a stearic acid dimer and sebacic acid. Sherwood et al., *Bio/Technology* 10: 1446 (1992). The rate of release of an immunoconjugate or antibody from such a matrix depends upon the molecular weight of the immunoconjugate or antibody, the amount of immunoconjugate, antibody within the matrix, and the size of dispersed particles. Saltzman et al., *Biophys. J.* 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The immunoconjugate, antibody fusion proteins, or naked antibody may also be administered to a mammal subcutaneously or even by other parenteral routes. Moreover, the administration may be by continuous infusion or by single or multiple boluses. In general, the dosage of an administered immunoconjugate, fusion protein or naked antibody for humans will vary depending upon such factors as the patient's age, weight, height, sex, general medical condition and previous medical history. Typically, it is desirable to provide the recipient with a dosage of immunoconjugate, antibody fusion protein or naked antibody that is in the range of from about 1 mg/kg to 20 mg/kg as a single intravenous infusion, although a lower or higher dosage also may be administered as circumstances dictate. This dosage may be repeated as needed, for example, once per week for 4-10 weeks, preferably once per week for 8 weeks, and more preferably, once per week for 4 weeks. It may also be given less frequently, such as every other week for several months. The dosage may be given through various parenteral routes, with appropriate adjustment of the dose and schedule.

For purposes of therapy, the immunoconjugate, fusion protein, or naked antibody is administered to a mammal in a therapeutically effective amount. A suitable subject for the present invention is usually a human, although a nonhuman animal subject is also contemplated. An antibody preparation is said to be administered in a "therapeutically effective amount" if the amount administered is physiologically significant. An agent is physiologically significant if its presence results in a detectable change in the physiology of a recipient mammal. In particular, an antibody preparation of the present invention is physiologically significant if its presence invokes an antitumor response or mitigates the signs and symptoms of an autoimmune disease state. A physiologically significant effect could also be the evocation of a humoral and/or cellular immune response in the recipient mammal.

Methods of Treatment

The present invention contemplates the use of naked anti-CD74 antibodies of the present invention as the primary composition for treatment of a CD74 expressing malignancy, where the disease or disorder is selected from the group consisting of an immune dysregulation disease, an autoimmune disease, organ graft rejection, and graft versus host disease. The CD74 expressing malignancy is selected from the group consisting of a solid tumor, non-Hodgkin's lymphoma, Hodgkin's lymphoma, multiple myeloma, another B-cell malignancy and a T-cell malignancy. The solid tumor is selected from the group consisting of a melanoma, carcinoma and sarcoma and the carcinoma is selected from the group consisting of a renal carcinoma, lung carcinoma, intestinal carcinoma, stomach carcinoma and melanoma. The B-cell malignany is selected from the group consisting of non-Hodgkins lymphoma, Hodkgin's lymphoma, indolent forms of B-cell lymphomas, aggressive forms of B-cell lymphomas, chronic lymphatic leukemias, acute lymphatic leukemias, and multiple myeloma, B-cell disorders and other diseases. In particular, the compositions described herein are particularly useful for treatment of various autoimmune as well as indolent forms of B-cell lymphomas, aggressive forms of B-cell lymphomas, chronic lymphatic leukemias, acute lymphatic leukemias, multiple myeloma, and Waldenström's macroglobulinemia. For example, the humanized anti-CD74 antibody components and immuno conjugates can be used to treat both indolent and aggressive forms of non-Hodgkin's lymphoma.

More specifically, the invention contemplates a method for treating a B-cell malignancy comprising administering to a subject with a B-cell related malignancy, a therapeutic composition comprising a pharmaceutically acceptable carrier and at least one humanized, chimeric, or human anti-CD74 mAb or fragment thereof or antibody fusion protein thereof of the present invention, wherein the B-cell malignancy is lymphoma or leukemia. More specifically, the B-cell malignancy is non-Hodgkin's lymphoma, indolent forms of B-cell lymphomas, aggressive forms of B-cell lymphomas, multiple myeloma, chronic lymphatic leukemias, or acute lymphatic leukemias. The CD74 mAb or fragment thereof is administered intravenously or intramuscularly at a dose of 20-2000 mg. The present method further comprises administering the anti-CD74 mAb or fragment thereof before, during or after the administration of at least one therapeutic agent used to treat the B-cell malignancy. The therapeutic agent comprises a naked antibody, an immunomodulator, a hormone, a cytotoxic agent, an enzyme, an antibody conjugated to at least one immunomodulator, radioactive label, hormone, enzyme, or cytotoxic agent, or a combination thereof. The immunomodulator preferably is a cytokine and said cytotoxic agent is a drug or toxin. The antibody that is administered incombination as a naked antibody or as a supplemental immunoconjugate is reactive with CD4, CD5, CD8, CD14, CD15, CD19, CD20, CD21, CD22, CD23, CD25, CD30, CD33, CD37, CD38, CD40, CD40L, CD46, CD52, CD54, CD80, CD126, B7, MUC1, Ia, HM1.24, tenascin, and HLA-DR, preferably a mature HLA-DR dimer, formulated in a pharmaceutically acceptable vehicle.

The invention also contemplates treating a malignancy comprising administering to a subject with a CD74 antigen-positive malignancy other than lymphoma or leukemia, a therapeutic composition comprising a pharmaceutically acceptable carrier and at least one anti-CD74 mAb or fragment thereof or an antibody fusion protein thereof as disclosed in the present invention. The anti-CD74 mAb or fragment thereof or an antibody fusion protein thereof is administered intravenously or intramuscularly at a dose of 20-2000 mg. Further, the anti-CD74 mAb or fragment thereof or an antibody fusion protein thereof is administered before, during or after the administration of at least one therapeutic agent used to treat the malignancy. The therapeutic agent, as described above and throughout the specification, comprises an antibody, an immunomodulator, a hormone, a cytotoxic agent, an antibody conjugated to at least one immunomodulator, radioactive label, enzyme, hormone, cytotoxic agent, antisense oligonucleotide, or a combination thereof, where the immunomodulator is a cytokine and said cytotoxic agent is a drug or toxin. When an antibody is administered in combination with the anti-CD74 mAb or fragment thereof to treat a malignancy that is not a B-cell malignancy, it should be reactive with a tumor marker other than CD74, expressed by the cells that comprise the malignancy that is treated, formulated in a pharmaceutically acceptable vehicle. Examples of antibodies that can be administered for malignant melanoma associated antigens are those antibodies reactive with MART-1, TRP-1, TRP-2 and gp100. Further, preferred antibodies to multiple myeloma-associated antigens are those reactive with MUC1 and CD38.

The compositions for treatment contain at least one humanized, chimeric or human monoclonal anti-CD74 antibody alone or in combination with other antibodies, such as other humanized, chimeric, or human antibodies, therapeutic agents or immunomodulators. In particular, combination therapy with a fully human antibody is also contemplated and is produced by the methods as set forth above.

Naked or conjugated antibodies to the same or different epitope or antigen may also be combined with one or more of the antibodies of the present invention. For example, a humanized, chimeric or human naked anti-CD74 antibody may be combined with another naked humanized, naked chimeric or naked human anti-CD74 mAb; a humanized, chimeric or human naked anti-CD74 antibody may be combined with an anti-CD74 immunoconjugate; a naked anti-CD74 antibody may be combined with an anti-CD22 radioconjugate; or an anti-CD22 naked antibody may be combined with a humanized, chimeric or human anti-CD74 antibody conjugated to an isotope, or one or more chemotherapeutic agents, cytokines, enzymes, toxins or a combination thereof. A fusion protein of a humanized, chimeric or human CD20 antibody and a toxin or immunomodulator, or a fusion protein of at least two different B-cell antibodies (e.g., a CD74 and a CD22 mAb, a CD20 mAb or a CD19 mAb) may also be used in this invention. Reference is made to pending U.S. Ser. No. 09/965,796 filed on Oct. 1, 2001, entitled "Immunotherapy of B-Cell Malignancies Using Anti-CD-22 Antibodies," which is a continuation of U.S. Pat. No. 6,306,393, both of which are incorporated in their entirety by reference, that discloses treatment with an anti-CD22 antibodies in combination with other naked antibodies. Many different antibody combinations, targeting at least two different antigens associated with B-cell disorders, as listed already above, may be constructed, either as naked antibodies or as partly naked and partly conjugated with a therapeutic agent or immunomodulator, or merely in combination with another therapeutic agents, such as a cytotoxic drug or with radiation.

As used herein, the term "immunomodulator" includes cytokines, stem cell growth factors, lymphotoxins, such as tumor necrosis factor (TNF), and hematopoietic factors, such as interleukins (e.g., interleukin-1 (IL-1), IL-2, IL-3, IL-6, IL-10, IL-12, IL-18, and IL-21), colony stimulating factors (e.g., granulocytecolony stimulating factor (G-CSF) and granulocyte macrophage-colony stimulating factor (GM-CSF)), interferons (e.g., interferons-α, -β and -γ), the stem cell growth factor designated "S1 factor," erythropoietin, thrombopoietin or a combination thereof Examples of suitable immunomodulator moieties include IL-1, IL-2, IL-3, IL-6, IL-10, IL-12, IL-18, IL-21, and a combination thereof, and interferon-γ, TNF-α, and the like. Alternatively, subjects can receive naked anti-CD74 antibodies and a separately administered cytokine, which can be administered before, concurrently or after administration of the naked anti-CD74 antibodies. As discussed supra, the anti-CD74 antibody may also be conjugated to the immunomodulator. The immunomodulator may also be conjugated to a hybrid antibody consisting of one or more antibodies binding to different antigens.

Multimodal therapies of the present invention further include immunotherapy with naked anti-CD74 antibodies supplemented with administration of anti-CD22, anti-CD19, anti-CD21, anti-CD20, anti-CD80, anti-CD23, anti-CD46 or HLA-DR, preferably the mature HLA-DR dimer antibodies in the form of naked antibodies, fusion proteins, or as immunoconjugates. These antibodies include polyclonal, monoclonal, chimeric, human or humanized antibodies that recognize at least one epitope on these antigenic determinants. Anti-CD19 and anti-CD22 antibodies are known to those of skill in the art. See, for example, Ghetie et al., *Cancer Res.* 48:2610 (1988); Hekman et al., *Cancer Immunol. Immunother.* 32:364 (1991); Longo, *Curro Opin. Oncol.* 8:353 (1996) and U.S. Pat. Nos. 5,798,554 and 6,187,287, incorporated in their entirety by reference.

In another form of multimodal therapy, subjects receive naked anti-CD74 antibodies, and/or immunoconjugates, in conjunction with standard cancer chemotherapy. For example, "CVB" (1.5 g/m$^2$ cyclophosphamide, 200-400 mg/m$^2$ etoposide, and 150-200 mg/m$^2$ carmustine) is a regimen used to treat non-Hodgkin's lymphoma. Patti et al., *Eur. J. Haematol.* 51: 18 (1993). Other suitable combination chemotherapeutic regimens are well-known to those of skill in the art. See, for example, Freedman et al., "Non-Hodgkin's Lymphomas," in CANCER MEDICINE, VOLUME 2, 3rd Edition, Holland et al. (eds.), pages 2028-2068 (Lea & Febiger 1993). As an illustration, first generation chemotherapeutic regimens for treatment of intermediate-grade non-Hodgkin's lymphoma (NHL) include C-MOPP (cyclophosphamide, vincristine, procarbazine and prednisone) and CHOP (cyclophosphamide, doxorubicin, vincristine, and prednisone). A useful second generation chemotherapeutic regimen is m-BACOD (methotrexate, bleomycin, doxorubicin, cyclophosphamide, vincristine, dexamethasone and leucovorin), while a suitable third generation regimen is MACOP-B (methotrexate, doxorubicin, cyclophosphamide, vincristine, prednisone, bleomycin and leucovorin). Additional useful drugs include phenyl butyrate and brostatin-1. In a preferred multimodal therapy, both chemotherapeutic drugs and cytokines are co-administered with an antibody, immunoconjugate or fusion protein according to the present invention. The cytokines, chemotherapeutic drugs and antibody or immunoconjugate can be administered in any order, or together.

In a preferred embodiment, NHL is treated with 4 weekly infusions of the humanized anti-CD74 antibody at a dose of 200-400 mg/m$^2$ weekly for 4 consecutive weeks or every-other week (iv over 2-8 hours), repeated as needed over next months/yrs. Also preferred, NHL is treated with 4 semimonthly infusions as above, but combined with epratuzumAb (anti-CD22 humanized antibody) on the same days, at a dose of 360 mg/m$^2$, given as an iv infusion over 1 hour, either before, during or after the anti-CD74 monoclonal antibody infusion. Still preferred, NHL is treated with 4 weekly infusions of the anti-CD74 antibody as above, combined with one or more injections of CD22 mAb radiolabeled with a therapeutic isotope such as yttrium-90 (at dose of Y$^{90}$ between 5 and 35 mCi/meter-square as one or more injections over a period of weeks or months.

In addition, a therapeutic composition of the present invention can contain a mixture or hybrid molecules of monoclonal naked anti-CD74 antibodies directed to different, non-blocking CD74 epitopes. Accordingly, the present invention contemplates therapeutic compositions comprising a mixture of monoclonal anti-CD74 antibodies that bind at least two CD74 epitopes. Additionally, the therapeutic composition described herein may contain a mixture of anti-CD74 antibodies with varying CDR sequences.

Although naked anti-CD74 antibodies are the primary therapeutic compositions for treatment of B cell lymphoma and autoimmune diseases, the efficacy of such antibody therapy can be enhanced by supplementing the naked antibodies, with supplemental agents, such as immunomodulators, like interferons, including IFNα, IFNβ and IFNγ, interleukins including IL-1, IL-2, IL-3, IL-6, IL-10, IL12, IL-15, IL-18, IL-21, and a combination thereof, and cytokines including G-CSF and GM-CSF. Accordingly, the CD74 antibodies can be combined not only with antibodies and cytokines, either as mixtures (given separately or in some predetermined dosing regiment) or as conjugates or fusion proteins to the anti-CD74 antibody, but also can be given as a combination with drugs or with antisense olignucleotides. For example, the anti-CD74 antibody may be combined with CHOP as a 4-drug chemotherapy regimen. Additionally, a naked anti-CD74 antibody may be combined with a naked anti-CD22 antibodies and CHOP or Fludarabine as a drug combination for NHL therapy. The supplemental therapeutic compositions can be administered before, concurrently or after administration of the anti-CD74 antibodies. The naked anti-CD74 mAb may also be combined with an antisense bcl oligonucleotide.

As discussed supra, the antibodies of the present invention can be used for treating B cell lymphoma and leukemia, and other B cell diseases or disorders as well as other malignancies in which affected or associated malignant cells are reactive with CD74. For example, anti-CD74 antibodies can be used to treat immune dysregulation disease and related autoimmune diseases, including Class-III autoimmune diseases such as immune-mediated thrombocytopenias, such as acute idiopathic thrombocytopenic purpura and chronic idiopathic thrombocytopenic purpura, dermatomyositis, Sjögren's syndrome, multiple sclerosis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, sarcoidosis, ulcerative colitis, erythema multiforme, IgA nephropathy, polyarteritis nodosa, ankylosing spondylitis, Goodpasture's syndrome, thromboangitis ubiterans, primary biliary cirrhosis, Hashimoto's thyroiditis, thyrotoxicosis, scleroderma, chronic active hepatitis, polymyositis/dermatomyositis, polychondritis, pamphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis and fibrosing alveolitis.

Particularly, the humanized, chimeric or human anti-CD74 mAbs or fragments thereof or antibody fusion proteins thereof of the present invention are administered to a subject with one or more of these autoimmune diseases. The anti-CD74 antibodies of the present invention are particularly useful in the method of treating autoimmune disorders, disclosed in pending U.S. Ser. No. 09/590,284 filed on Jun. 9, 2000 entitled "Immunotherapy of Autoimmune Disorders using Antibodies that Target B-Cells," which is incorporated in its entirety by reference. Preferably the anti-CD74 mAb or fragment thereof or an antibody fusion protein thereof is administered intravenously or intramuscularly at a dose of 20-2000 mg. Further, the anti-CD74 mAb or fragment thereof or an antibody fusion protein thereof is administered before, during or after the administration of at least one therapeutic agent used to treat the disorder. The therapeutic agent, as described above and throughout the specification, comprises an antibody, an immunomodulator, a hormone, an enzyme, a cytotoxic agent, an antibody conjugated to at least one immunomodulator, radioactive label, hormone, enzyme, or cytotoxic agent, antisense oligonucleotide or a combination thereof, where the immunomodulator is a cytokine and said cytotoxic agent is a drug or toxin. The antibody that is administered incombination as a naked antibody or as a supplemental immunoconjugate is reactive with CD4, CD5, CD8, CD14, CD15, CD19, CD20, CD21, CD22, CD23, CD25, CD30, CD33, CD37, CD38, CD40, CD40L, CD46, CD52, CD54, CD80, CD126, B7, MUC1, Ia, HM1.24, tenascin, and mature HLA-DR, preferably a mature HLA-DR dimer, formulated in a pharmaceutically acceptable vehicle.

A further method for treating one of the diseases selected from the group consisting of lymphoma, leukemia, myeloma, other CD74-expressing malignancies, immune dysregulation disease, autoimmune disease and a combination thereof, comprising administering a therapeutic composition comprising a pharmaceutically acceptable carrier and at least one anti-CD74 mAb or fragment thereof or an antibody fusion protein thereof of the present invention, wherein at least one therapeutic agent is linked to the mAb or fragment thereof or the Fvs or Fab's of the antibody fusion protein thereof by chemical conjugation or by genetic fusion. The therapeutic agent may be an immunomodulator, a radioactive label, a hormone, an enzyme, or a cytotoxic agent, and the immunomodulator is a cytokine and said cytotoxic agent is a drug or toxin.

Anti-CD74 antibodies may also induce apoptosis in cells expressing the CD74 antigen. Evidence of this induction is supported in the examples of the present invention. Other antibodies have demonstrated that apoptosis could be induced using lymphoid cells that have Fc-receptors reactive with the IgG 1-Fc of CD20 MAbs that crosslinked. See Shan et al., *Cancer Immunol. Immunother.* 48(12):673-683 (2000). Further, it was reported that aggregates of a chimeric CD20 MAb, i.e., homopolymers, induced apoptosis. See Ghetie et al., Blood 97(5): 1392-1398 (2000) and Ghetie et al., Proc. Natl. Acad. Sci USA 94(14): 7509-7514 (1997).

Antibodies specific to the CD74 surface antigen of B cells can be injected into a mammalian subject, which then bind to the CD74 cell surface antigen of both normal and malignant B cells. A mammalian subject includes humans and domestic animals, including pets, such as dogs and cats. The anti-CD74 mAbs of the present invention, i.e., humanized, chimeric, human, caninized and felinized, and even murine anti-CD74 mAbs, can be used to treat the nonhuman mammalian subjects when there is a species cross reactivity for the CD74 antigen. The murine mAbs, which are immunogenic in humans, are usually less immunogenic in non-human mammalian subjects. The anti-CD74 antibody bound to the CD74 surface antigen leads to the destruction and depletion of neoplastic B cells.

Method of Diagnosis

Also provided for in the present invention is a method of diagnosing a disease in a subject, diagnosed with or suspected of having at least one of the diseases selected from the groups consisting of lymphoma, leukemia, myeloma, other CD74-expressing malignancies, immune dysregulation disease, autoimmune disease and a combination thereof, comprising administering to said subject a diagnostically effective amount of a diagnostic conjugate a pharmaceutically acceptable carrier and at least one anti-CD74 mAb or fragment thereof or antibody fusion protein thereof, wherein a diagnostic agent is linked to the mAb or fragment thereof or the Fvs or Fabs of the antibody fusion protein thereof by chemical conjugation and detecting the diagnostic agent. Diagnostic agents useful in the present invention are a radioisotope, wherein the photons of the radioisotope are detected by radioscintigrapy or PET, or a metal that can be detected by MRI, or a liposome or gas filled liposome, and wherein the liposome can be detected by an ultrasound scanning device.

The internalization of murine anti-CD74 mAb, chimeric anti-CD74 mAb and humanized anti-CD74 mAb into target cells can be followed by fluorescence labeling, essentially according to the procedure of Pirker et al., J. Clin. Invest., 76:1261 (1985), which is incorporated by reference. Cultured Raji cells are centrifuged and the cells resuspended in fresh medium to a concentration of about $5 \times 10^6$ cells/ml. To each well of a 96-well microtiter plate, 100 µl of the cell suspension is added. The antibodies, 40 µg/ml, in a volume of 100 µl are added to the reaction wells at timed intervals so as to terminate all reactions simultaneously. The plate is incubated at 37° C. in a $CO_2$ cell culture incubator. Unbound antibodies are removed by washing the cells three times with cold 1% FCS/PBS at the end of the incubation. The cells are then treated with 1 ml of Formaid-Fresh [10% formalin solution (Fisher, Fair Lawn, N.J.)] for 15 min at 4° C. After washing, antibodies present either on the cell surface or inside the cells are detected by treatment with FITC-labeled goat anti-mouse antibody (Tago, Burlingame, Calif.), or FITC-labeled goat anti-human antibody (Jackson ImmunoResearch, West Grove, Pa.), depending on whether the antibody being assayed for is murine, chimeric, or humanized, respectively. Fluorescence distributions are evaluated using a BH-2 fluorescence microscope (Olympus, Lake Success, N.Y.).

In a related vein, a method for screening/diagnosing bone cancers is described in Juweid et al., 1999, could benefit from the superior anti-CD74 mAbs of the present invention. Accordingly, a method comprising $^{99m}$Tc-labeled humanized or chimeric anti-CD74 mAb is contemplated.

Expression Vectors

The DNA sequence encoding a humanized, chimeric or human anti-CD74 mAb. More specifically the DNA sequence comprises a nucleic acid encoding a mAb or fragment thereof selected from the group consisting (a) an anti-CD74mAb or fragment described herein, (b) an immunoconjugate comprising anyone of the anti-CD74 mAbs or fragment thereof described herein, (c) an antibody fusion protein or fragment thereof comprising at least two of said anti-CD74 mAbs or fragments thereof described herein; (d) an antibody fusion protein or fragment described herein; (e) a vaccine as described herein; and a bispecific or multispecific antibody described herein. Any of the DNA sequences of the present invention can be recombinantly engineered into a variety of known host vectors that provide for replication of the nucleic acid. These vectors can be designed, using known methods, to contain the elements necessary for directing transcription, translation, or both, of the nucleic acid in a cell to which it is delivered. Known methodology can be used to generate expression constructs the have a protein-coding sequence operably linked with appropriate transcriptional/translational control signals. These methods include in vitro recombinant DNA techniques and synthetic techniques. For example, see Sambrook et al., 1989) MOLECULAR CLONING: A LABORATORY MANUAL, Cold Spring Harbor Laboratory (New York); Ausubel et al., 1997, CURRENT PROTOCOLS IN MOLECULAR BIOLOGY, John Wiley & Sons (New York). Also provided for in this invention is the delivery of a polynucleotide not associated with a vector.

Vectors suitable for use in the instant invention can be viral or non-viral. Particular examples of viral vectors include adenovirus, AAV, herpes simplex virus, lentivirus, and retrovirus vectors. An example of a non-viral vector is a plasmid. In a preferred embodiment, the vector is a plasmid.

An expression vector, as described herein, is a polynucleotide comprising a gene that is expressed in a host cell. Typically, gene expression is placed under the control of certain regulatory elements, including constitutive or inducible promoters, tissue-specific regulatory elements, and enhancers. Such a gene is said to be "operably linked to" the regulatory elements. Preferred expression vectors are the pdHI2 and GS vector.

Preferably, the expression vector of the instant invention comprises the DNA sequence encoding a humanized, chimeric or human anti-CD74 mAb, which includes both the heavy and the light chain variable and constant regions. However, two expression vectors may be used, with one comprising the heavy chain variable and constant regions and the other comprising the light chain variable and constant regions. Still preferred, the expression vector further comprises a promoter. Because any strong promoter can be used, a DNA sequence encoding a secretion signal peptide, a genomic sequence encoding a human IgG1 heavy chain constant region, an Ig enhancer element and at least one DNA sequence encoding a selection marker.

The method for the expression of an anti-CD74mAb or fragment thereof or antibody fusion protein or fragment thereof employing the present invention comprises: (a) transfecting a host cell with a DNA sequence encoding an anti-CD74 mAb or fragment thereof or an immunoconjugate, fusion protein or bispecific or multispecific antibody thereof; and (b) culturing the cell secreting the antiCD74 mAb or fragment thereof or antibody fusion protein or fragment thereof. The host cell is derived from bacterial, yeast or mammalian cells. More preferably from a mammalian cells, which in one embodiment is a lymphocyctic cell, such as a myeloma cell.

Also contemplated herein is a method for expressing a humanized anti-CD74 mAb, comprising (i) linearizing at least one expression vector comprising a DNA sequence encoding a humanized, chimeric, or human anti-CD74 mAb, (ii) transfecting mammalian cells with at least one of said linearized vector, (iii) selecting transfected cells which express a marker gene, and (iv) identifying the cells secreting the humanized anti-CD74 mAb from the transfected cells.

The inventors have isolated cDNAs encoding the VL and VH regions of the murine anti-CD74 monoclonal antibody (mLL1 mAb) and recombinantly subcloned them into mammalian expression vectors containing the genes encoding kappa and IgG1 constant regions, respectively, of human antibodies. Cotransfection of mammalian cells with these two recombinant DNAs expressed a chimeric antiCD74 mAb (cLL1) that, like the parent mLL1 mAb, bound avidly to, and was rapidly internalized by, B-lymphoma cells.

The CDRs of the VK and VH DNAs have been similarly recombinantly linked to the framework (FR) sequences of the human VK and VH regions, respectively, which are subsequently linked, respectively, to the human kappa and IgG1 constant regions, so as to express in mammalian cells as described above a humanized anti-CD74 mAb (hLL1).

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

The antibody described herein is a monoclonal antibody (mAb). Monoclonal antibodies are a homogeneous population of antibodies to a particular antigen and the antibody comprises only one type of antigen binding site to which the nucleic acid specifically binds. Rodent monoclonal antibodies to specific antigens may be obtained by methods known to those skilled in the art. See, for example, Kohler and Milstein, *Nature* 256: 495 (1975), and Coligan et al. (eds.), CURRENT PROTOCOLS IN IMMUNOLOGY, VOL. 1, pages 2.5.1-2.6.7 (John Wiley & Sons 1991) [hereinafter "Coligan"]. Briefly, monoclonal antibodies can be obtained by injecting mice with a composition comprising an antigen, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL 10, pages 79-104 (The Humana Press, Inc. 1992).

Method of Making

The VK and VH sequences for chimeric or humanized anti-CD74 mAb can amplified by PCR as described by Orlandi et al., (Proc. Natl. Acad. Sci., USA, 86: 3833 (1989)) which is incorporated by reference. VK sequences may be amplified using the primers CK3BH and VK5-3 (Leung et al., BioTechniques, 15: 286 (1993), which is incorporated by reference), while VH sequences can be amplified using the primer CH1B which anneals to the CH1 region of murine IgG, and VHIBACK (Orlandi et al., 1989 above). The PCR reaction mixtures containing 10 µl of the first strand cDNA product, 9 µl of 10×PCR buffer [500 mM KCl, 100 mM Tris-HCl (pH 8.3), 15 mM MgCl2, and 0.01% (w/v) gelatin] (Perkin Elmer Cetus, Norwalk, Conn.), can be subjected to 30 cycles of PCR. Each PCR cycle preferably consists of denaturation at 94° C. for 1 min, annealing at 50° C. for 1.5 min, and polymerization at 72° C. for 1.5 min. Amplified VK and VH fragments can be purified on 2% agarose (BioRad, Richmond, Calif.). See Example 3 for a method for the synthesis of an oligo A (149-mer) and an oligo B (140-mer) on an automated Cyclone Plus DNA synthesizer (Milligan-Biosearch) for use in constructing humanized V genes.

PCR products for VK can be subcloned into a staging vector, such as a pBR327-based staging vector VKpBR that contains an Ig promoter, a signal peptide sequence and convenient restriction sites to facilitate in-frame ligation of the VK PCR products. PCR products for VH can be subcloned into a similar staging vector, such as the pBluescript-based VHpBS. Individual clones containing the respective PCR products may be sequenced by, for example, the method of Sanger et al., *Proc. Natl. Acad. Sci., USA,* 74: 5463 (1977) which is incorporated by reference.

The DNA sequences described herein are to be taken as including all alleles, mutants and variants thereof, whether occurring naturally or induced.

The two plasmids can be co-transfected into an appropriate cell, e.g., myeloma Sp2/0-Ag 14, colonies selected for hygromycin resistance, and supernatant fluids monitored for production of chimeric or humanized anti-CD74 mAbs by, for example, an ELISA assay, as described below.

Transfection, and assay for antibody secreting clones by ELISA, can be carried out as follows. About 10 μg of hLL1 pKh (light chain expression vector) and 20 μg of hLL1pG1g (heavy chain expression vector) can be used for the transfection of $5 \times 10^6$ SP2/0 myeloma cells by electroporation (Bio-Rad, Richmond, Calif.) according to Co et al., *J. Immunol.,* 148: 1149 (1992) which is incorporated by reference. Following transfection, cells may be grown in 96-well microtiter plates in complete HSFM medium (GIBCO, Gaithersburg, Md.) at 37° C., 5% $CO_2$. The selection process can be initiated after two days by the addition of hygromycin selection medium (Calbiochem, San Diego, Calif.) at a final concentration of 500 μg/ml of hygromycin. Colonies typically emerge 2-3 weeks post-electroporation. The cultures can then be expanded for further analysis.

Transfectoma clones that are positive for the secretion of chimeric or humanized heavy chain can be identified by ELISA assay. Briefly, supernatant samples (100 μl) from transfectoma cultures are added in triplicate to ELISA microtiter plates precoated with goat anti-human (GAH)-IgG, $F(ab')_2$ fragment-specific antibody (Jackson ImmunoResearch, West Grove, Pa.). Plates are incubated for 1 h at room temperature. Unbound proteins are removed by washing three times with wash buffer (PBS containing 0.05% polysorbate 20). Horseradish peroxidase (HRP) conjugated GAH-IgG, Fc fragment-specific antibodies (Jackson ImmunoResearch, West Grove, Pa.) are added to the wells, (100 μl of antibody stock diluted$\times 10^4$, supplemented with the unconjugated antibody to a final concentration of 1.0 μl/ml). Following an incubation of 1 h, the plates are washed, typically three times. A reaction solution, [100 μl, containing 167 μg of orthophenylene-diamine (OPD) (Sigma, St. Louis, Mo.), 0.025% hydrogen peroxide in PBS], is added to the wells. Color is allowed to develop in the dark for 30 minutes. The reaction is stopped by the addition of 50 μl of 4 N HCl solution into each well before measuring absorbance at 490 nm in an automated ELISA reader (Bio-Tek instruments, Winooski, Vt.). Bound chimeric antibodies are than determined relative to an irrelevant chimeric antibody standard (obtainable from Scotgen, Ltd., Edinburg, Scotland).

Antibodies can be isolated from cell culture media as follows. Transfectoma cultures are adapted to serum-free medium. For production of chimeric antibody, cells are grown as a 500 ml culture in roller bottles using HSFM. Cultures are centrifuged and the supernatant filtered through a 0.2 micron membrane. The filtered medium is passed through a protein A column (1×3 cm) at a flow rate of 1 ml/min. The resin is then washed with about 10 column volumes of PBS and protein A-bound antibody is eluted from the column with 0.1 M glycine buffer (pH 3.5) containing 10 mM EDTA. Fractions of 1.0 ml are collected in tubes containing 10 μl of 3 M Tris (pH 8.6), and protein concentrations determined from the absorbancy at 280/260 nm. Peak fractions are pooled, dialyzed against PBS, and the antibody concentrated, for example, with the Centricon 30 (Amicon, Beverly, Mass.). The antibody concentration is determined by ELISA, as before, and its concentration adjusted to about 1 mg/ml using PBS. Sodium azide, 0.01% (w/v), is conveniently added to the sample as preservative.

All published articles and patents, as well as filings of patents cited herein are incorporated in their entirety by reference. The invention is further described by reference to the following examples, which are provided for illustration only. The invention is not limited to the examples but rather includes all variations that are evident from the teachings provided herein.

EXAMPLES

Example 1

Molecular Cloning and Sequence Elucidation for LL1 Heavy and Light Chain Variable Regions The V gene of mLL1 was obtained by RT-PCR using VK5'-4 and VK1FOR primers as described by Leung et al. 1993 and Orlandi et al. (PNAS 86:3833-3837. (1989), respectively, and cloned into pCR2.1 AT-cloning vector (Invitrogen). Multiple clones were sequenced to eliminate possible errors resulted from PCR reaction. Majority of clones (6) contained an identical murine V sequence, which was designated as LL1V and the sequence is shown in FIG. 1B. Comparison with other mouse Vk sequences revealed LL1Vk is a member of the kappa light chain subclass II.

Since RT-PCR failed to yield a full-length sequence encoding a mouse VH gene, the second cloning approach, rapid amplification of cDNA 5'-ends (5'-RACE) was employed. The adaptor-ligated cDNA prepared from LL1 hybridoma cells was amplified by PCR using a universal anchor primer (Life Technologies) and a gene specific primer, CH-1B (Leung et al. 1994), which anneals to the CH1 region of murine heavy chain. The major PCR species of ~650 by resulted from PCR was cloned into pCR2.1 AT-cloning vector and multiple clones were sequenced by DNA sequencing. The PCR product contained a full-length VH sequence (FIG. 1A) flanked by the sequences of non-coding and secretion signal peptide at '5-end and partial coding sequence for the CH1 domain of 1 chain. No defective mutation was found within the sequence encoding the VH, which was designated as LL1VH. Comparison of hLL1VH with other mouse VH sequences revealed that it belonged to mouse heavy chain subgroup miscellaneous (Kabat et al., 1991). By comparing the amino acid sequences of LL1VH and V with murine Ab V genes in Kabat database and following Kabat's definition, the CDR regions of hLL1VH and Vk were identified as shown in FIGS. 1A and B, respectively. By comparing the amino acid sequences of LL1VH and V with murine Ab V genes in Kabat database and following Kabat's definition, the CDR regions of hLL1VH and Vk were identified as shown in FIGS. 1A and B, respectively.

Example 2

Construction of the Expression Vector for Chimeric LL1

To evaluated the authenticity of the cloned Fv for LL1, a chimeric LL1 (cLL1) was constructed and expressed. The nucleotide residues 7-12 of LL1Vk were modified to a PvuII restriction site, CAGCTG, by PCR with primers LL1VK-PvuII and VK1 FOR. The resulting PCR product was digested with PvuII and BglII (partially, due to the presence of an internal BglII site in the Vk) and force-cloned into a pBR327-based staging vector (digested with PvuII and BclI), VKpBR2, which contained same Ig promoter, signal peptide sequence and convenient restriction sites to facilitate in-frame ligation of the VK PCR product as used by Orlandi et al., 1989 and Leung et al., 1994.

```
LL1VK-PvuII
                                       (SEQ ID NO: 23)
5'GAT GTT CAG CTG ACC CAA ACT CCA CTC TCC-3'
```

Similarly, the nucleotide sequences at positions 10-15 and 345-351 of LL1VH were converted to PstI and BstEII, respectively, by PCR with primers LL1 B-1 and LL1F-1. The VH PCR product was then digested with PstI and BstEII and ligated into PstI and BstEII digested VHpBS2, a pBluescript-based staging vector containing a signal peptide sequence and convenient restriction sites to facilitate in-frame ligation of the VH PCR product {Orlandi, Gussow, et al., 1989 741/id}, modified from VHpBS (Leung, S. O., Shevitz, J., Pellegrini, M. C., Dion, A. S., Shih, L. B., Goldenberg, D. M., and Hansen, H. J. (1994)).

```
LL1B-1
                                       (SEQ ID NO: 24)
5'-CAG ATC CAG CTG CAG CAG TCT GGA CCT GAG-3'

LL1F-1
                                       (SEQ ID NO: 25)
5'-GA GAC GGT GAC CAG AGT CCC TTG GCC CCA A-3'
```

The sequences of both cLL1VH and Vk were confirmed by DNA sequencing and shown in FIGS. 2A and 2B, respectively.

The fragment containing the Vk sequences of cLL1, together with the signal peptide sequences, were excised from LL1VKpBR2 by double restriction digestion with XbaI and BamHI. The ~550 by Vk fragments was then subcloned into the XbaI/BamHI site of a mammalian expression vector, pdHL2. The resulting vector designated as cLL1VkpdHL2. Similarly, the ca. 750 by fragments containing the LL1VH, together with the signal peptide sequences, were excised from LL1VHpBS2 by XhoI and BamHI digestion and isolated by electrophoresis in an agarose gel. The fragment was subcloned into the XhoI and HindIII site of cLL1VkpdHL2 with the aid of linker comparable to both BamHI and HindIII ends, resulting in the final expression vectors, designated as cLL1pdHL2.

Example 3

Transfection and Expression of cLL1

Approximately 30 μg of cLL1pdHL2 was linerized by digestion with SalI and transfected into Sp2/0-Ag14 cells by electroporation. The transfected cells were plated into 96-well plate for 2 days and then selected for MTX resistance. Supernatants from colonies surviving selection were monitored for chimeric antibody secretion by ELISA assay. Positive cell clones were expanded and cLL1 was purified from cell culture supernatant by affinity chromatograpgy on a Protein A column.

Example 4

Binding Activity Assays

A competition cell binding assay was carried out to assess the immunoreactivity of cLL1 relative to the parent mLL1. A constant amount of $^{125}$I-labeled mLL1 (100,000 cpm) was incubated with Raji cells in the presence of varying concentrations of cLL1 or mLL1 at 4° C. for 1-2 h. The radioactivity associated with cells was determined after washing. As shown in FIG. 5, cLL1 antibody exhibited comparable binding activity as that of mLL1, confirming the authenticity of the cloned V genes.

The results were confirmed by a second competition assay based on flow cytometry. Briefly, using Raji cells as before and varying the concentration of one antibody relative to other, as before, the amount of bound mLL1 or cLL1 was determined with FITC-labeled anti-mouse Fc or anti-human Fc antibodies followed by analysis using flow cytometry.

An ELISA competitive binding assay were carried out in Raji cell membrane coated plate to assess the immunoreactivity of cLL1 relative to the parent mLL1. Raji cell membrane fraction was prepared by sonication and centrifugation. The crude membrane extracts were coated in 96-well flat bottomed PVC plate by centrifugation and fixed with 0.1% glutaraldehyde. Constant amount of the biotinylated mLL1 mixed with varying concentrations of mLL1 or cLL1 was added to the membrane coated wells and incubated at room temperature for 1-2 h. After washing, HRP-conjugated streptavidin was added and incubated for 1 h at room temperature. The amount of HRP-conjugated streptavidin bound to the membrane-bound biotinylated mLL1 was revealed by reading A490 nm after the addition of a substrate solution containing 4 mM orthophenylenediamine dihydrochloride and 0.04% $H_2O_2$.

Example 5

Choice of Human Frameworks and Sequence Design for the Humanization of LL1 Monoclonal Antibody By comparing the variable (V) region framework (FR) sequences of cLL1 to that of human antibodies in the Kabat data base, the FRs of cLL1VH and Vk were found to exhibit the highest degree of sequence homology to that of the human antibodies, RF-TS3 VH and HF-21/28 Vk, respectively. The amino acid sequences of are provided in FIGS. 3A and 3B and are compared with the cLL1VH and Vk sequences. Therefore, the FRs of RF-TS3 VH and the HF-21/28 Vk and FRs were selected as the human frameworks onto which the CDRs for LL1 VH and Vk were grafted, respectively. The FR4 sequence of NEWM, however, rather than that of RF-TS3, was used to replace the RF-TS3 FR4 sequence for the humanization of LL1 heavy chain. See FIG. 3A. A few amino acid residues in the LL1 FRs that are close to the putative CDRs were maintained in hLL1 based on the guideline described previously (Qu et aL, Clin. Cancer Rec. 5:3095s-3100s (1990)). These residues are L46, F87 and Q100 of VK (FIG. 3B) and I36, K37, Q46, A68, F91 and S93 of VH (FIG. 3A).

FIGS. 3A and 3B compare the human, chimeric and humanized VH and Vk amino acid sequences. The dots indicate the residues in the cLL1 and hLL1 that are identical to the corresponding residues in the human VH and Vk sequences. The DNA and amino acid sequences of hLL1 VH and Vk are shown in FIGS. 4A and 4B, respectively.

Example 6

PCR/Gene Synthesis of the Humanized V Genes

A modified strategy as described by Leung et al. (Leung et al, 1994) was used to construct the designed VK and VH genes for hLL1 using a combination of long oligonucleotide synthesis and PCR as illustrated in FIG. 5. For the construction of the hLL1 VH domain, two long oligonucleotides, hLL1VHA (176 mer) and hLL1VHB (165-mer) were synthesized on an automated DNA synthesizer (Applied Biosystem). The hLL1VHA sequence represents nt 20 to 195 of the hLL1VH domain:

(SEQ ID NO: 26)
5'-GGTCTGAGTT GAAGAAGCCT GGGGCCTCAG TGAAGGTTTC

CTGCAAGGCT TCTGGATACA CCTTCACTAA CTATGGAGTG

AACTGGATAA AGCAGGCCCC TGGACAAGGG CTTCAGTGGATGGGCTG

GAT AAACCCCAAC ACTGGAGAGC CAACATTTGA TGATGACTTC

AAGGGA-3'

The hLL1 VHB sequence represents the minus strand of the hLL1 VH domain complementary to nt 173 to 337:

(SEQ ID NO: 27)
5'-TCCCTTGGCC CCAATAAGCA AACCAGGCTT CGTTTTTACC

CCTCGATCTT GAACAGAAAT ACACGGCAGT GTCGTCAGCC

TTTAGGCTGC TGATCTGGAG ATATGCCGTG CTGACAGAGG

TGTCCAAGGA GAAGGCAAAT CGTCCCTTGA AGTCATCATC

AAATG-3'

The 3'-terminal sequences (22 nt residues) of hLL1 VHA and B are complementary to each other. Under defined PCR condition, 3'-ends of hLL1 VHA and B anneal to form a short double stranded DNA flanked by the rest of the long oligonucleotides. Each annealed end serves as a primer for the transcription of the single stranded DNA, resulting in a double strand DNA composed of the nt 20 to 337 of hLL1 VH. This DNA was further amplified in the presence of two short oligonucleotides, hLL1VHBACK and hLL1VHFOR to form the full-length hLL1VH.

hLL1VHBACK
(SEQ ID NO: 28)
5'-GTG GTG CTG CAG CAA TCT GGG TCT GAG TTC AAG AAG

CT-3' hLL1VHFOR
(SEQ ID NO: 29)
5'-AAG TGG ATC CTA TAA TCA TTC CTA GGA TTA ATG-3'.

Minimum amount of hLL1VHA and B (determined empirically) was amplified in the presence of 10 μl of 10×PCR Buffer (500 mM KCl, 100 mM Tris-HCl buffer, pH 8.3, 15 mM MgCl₂), 2 mol of hLL1VHBACK and hLL1VHFOR, and 2.5 units of Taq DNA polymerase (Perkin Elmer Cetus, Norwalk, Conn.). This reaction mixture was subjected to 3 cycles of PCR reaction consisting of denaturation at 94° C. for 1 minute, annealing at 45° C. for 1 minute, and polymerization at 72° C. for 1.5 minutes, and followed by 27 cycles of PCR reaction consisting of denaturation at 94° C. for 1 minute, annealing at 55° C. for 1 minute, and polymerization at 72° C. for 1 minute. Double-stranded PCR-amplified product for hLL1VH was gel-purified, restriction-digested with Pst1and BstEII and cloned into the complementary Pst1/BstEII sites of the heavy chain staging vector, VHpBS2.

For constructing the full length DNA of the humanized VK sequence, hLL1VKA (159-mer) and hLL1VKB (169-mer) were synthesized as described above. hLL1VKA and B were amplified by two short oligonucleotides hLL1VKBACK and hLL1VKFOR as described above.

The hLL1 VHA sequence represents nt 16 to 174 of the hLL1VH domain.

(SEQ ID NO: 30)
5'-CAGTCTCCAC TCTCCCTGCC CGTCACCCTT GGACAGCCGG

CCTCCATCTC CTGCAGATCA AGTCAGAGCC TTGTACACAG

AAATGGAAAC ACCTATTTAC ATTGGTTTCA GCAGAGGCCA

GGCCAATCTC CAAGGCTCCT GATCTACACA GTTTCCAAC-3'

The hLL1VHB sequence represents the minus strand of the hLL1VH domain complementary to nt 153 to 321.

(SEQ ID NO: 31)
5'-TGTCCCAGCA CCGAACGTGG GAGGAACATG TGAACTTTGA

GAGCAGAAAT AAACCCCAAC ATCCTCAGCC TCCACCCTGC

TGATTTTCAG TGTGAAATCA GTGCCTGACC CACTGCCGCT

GAATCTGTCT GGGACCCCAG AAAATCGGTT GGAAACTGTG

TAGATCAGG-3'.

hLL1VKBACK
(SEQ ID NO: 32)
5'-GAT GTT CAG CTG ACT CAG TCT CCA CTC TCC CTG-3' hLL1VKFOR
(SEQ ID NO: 33)
5'-G TTA GAT CTC CAG TCG TGT CCC AGC ACC GAA

CG-3'.

Gel-purified PCR products for hLL1Vk were restriction-digested with PvuII and Bg1III and cloned into the complementary PvuI/BclI sites of the light chain staging vector, VKpBR2. The final expression vector hLL1pdHL2 was constructed by sequencially subcloning the Xba1-BamHI and XhoI/BamHI fragments of hLL1Vk and VH, respectively, into pdHL2 as described above.

Example 7

Transfection, Expression and Binding Activity Assays for hLL1

The methods for expression and binding activity assays for hLL1 were same as described for cLL1.

Figure 7:
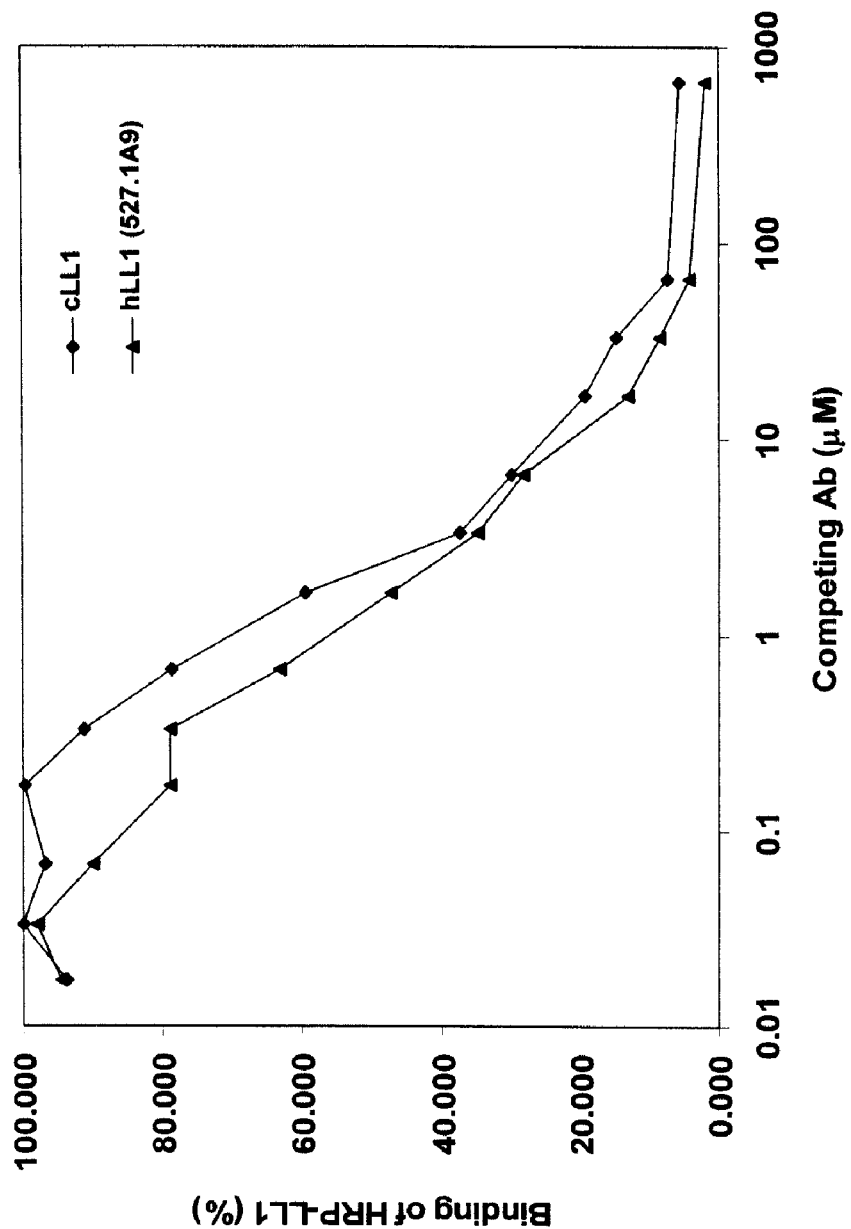
FIG. 7 shows the result of a competitive binding assay in Raji cell membrane coated micro wells to compare the binding affinity of hLL1 with that of cLL1. Varying concentrations of hLL1 (triangles) or cLL1 (diamonds) were mixed with a constant amount of HRP conjugated LL1 and incubated in 96-well microtitration plate coated with Raji membrane extracts at room temperature for 1 h. The membrane bound HRP-LL1 was measured. hLL1 and cLL1 competed equally well for the binding of HRP-LL1, indicating the binding specificity and affinity of mAb LL1 are preserved in the humanized LL1.

An ELISA competitive binding assay using Raji cell membrane extract coated plate was developed to assess the immunoreactivity of hLL1. Raji cell membrane fraction was prepared by sonication and centrifugation. The crude membrane extracts were coated in 96-well flat bottomed PVC plate by centrifugation and fixed with 0.1% glutaraldehyde. Constant amount of the biotinylated mLL1 mixed with varying concentrations of mLL1 or cLL1 was added to the membrane coated wells and incubated at room temperature for 1-2 h. After washing, HRP-conjugated streptavidin was added and incubated for 1 h at room temperature. The amount of HRP-conjugated streptavidin bound to the membrane bound biotinylated mLL1 was revealed by reading $A_{490\,nm}$ after the addition of a substrate solution containing 4 mM orthophenylenediamine dihydrochloride and 0.04% $H_2O_2$. As shown by the competition assays in FIG. 6, mLL1 and cLL1 antibodies exhibited similar binding activities. Likewise, the competition assays in FIG. 7, hLL1 and cLL1 antibodies exhibited similar binding activities.

Example 8

Internalization of hLL1

Figure 8:
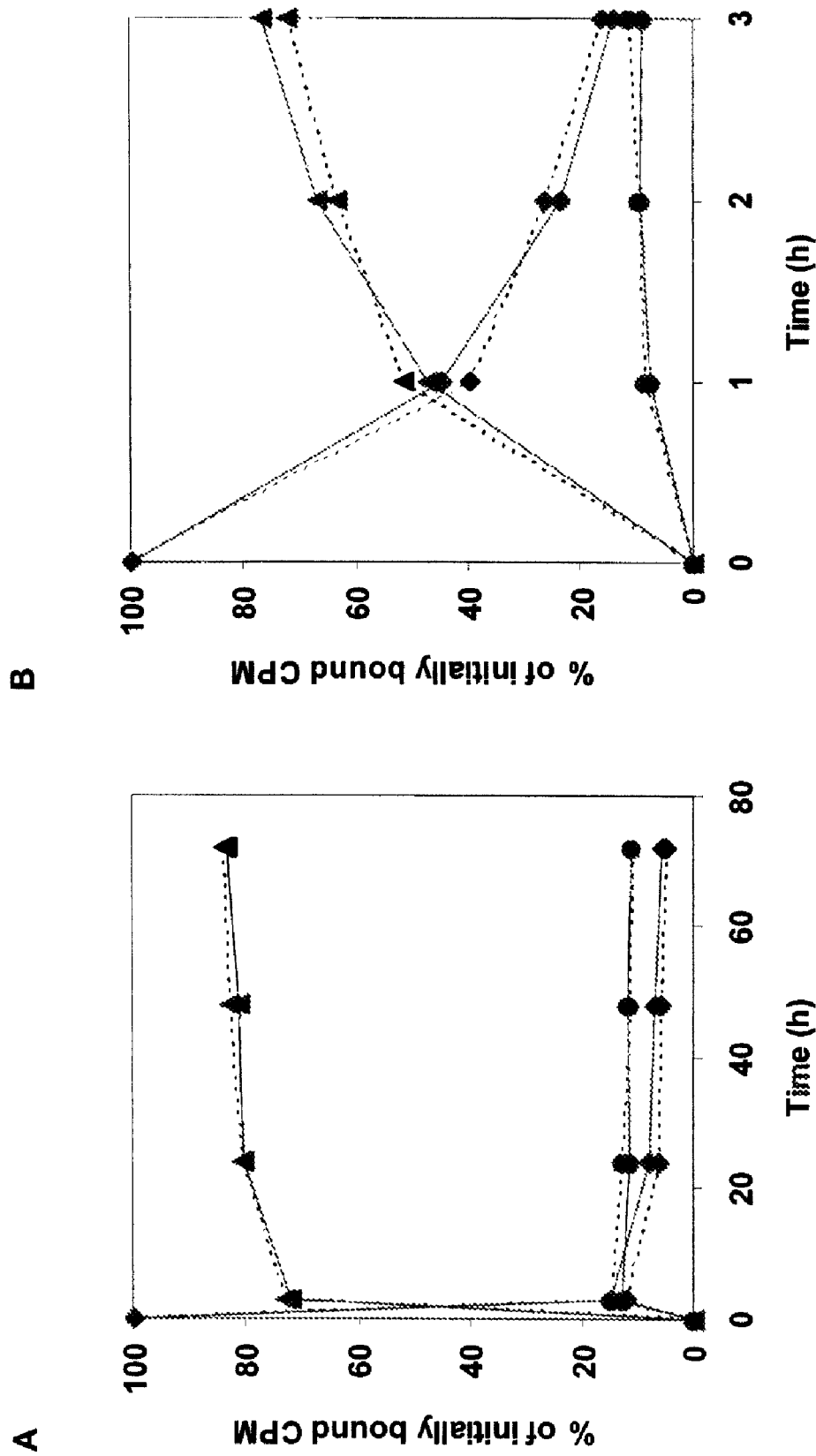
FIG. 8 shows the fate of $^{125}$I-labeled hLL1 and mLL1 bound to the surface of Raji cells. The radiolabeled hLL1 (solid line with symbols) or mLL1 (dotted line with symbols) was incubated with Raji cells and unbound Abs were removed by washing. The cells were then cultured as normal and the radiolabeled Abs associated with cells (diamond lines), secreted into medium (triangle lines) or degraded (circle lines) were measured at indicated time point.

Standard antibody processing assay was used to evaluate the internalization and metabolism of hLL1 in Raji cells (Hansen et al., 1996). Cells ($10^7$) were incubated in 1 ml of tissue culture medium containing $^{125}$I-labeled hLL1 or LL1 ($10^7$ cpm) for 1 h at 37° C. To ensure the specificity of Ab binding, controls of 1/10 sample size (cells, radioactivity and medium) were set up in every experiment with and without excess unlabeled Ab (a final concentration of 100 µg/ml). After the binding incubation, unbound radioactivity was removed by washing. The specificity controls were counted. In all experiments, the binding of radioactivity to cells was at least 90% blocked by the unlabeled Ab. The cells were then resuspended in 30 ml of fresh medium and dispensed in a 24-well plate with 1.5 ml/well. Samples of 1.5 ml were saved for radioactivity determination, which was the initially bound cpm. The plate was incubated in a $CO_2$ incubator. At 3, 24, 48, and 72 h, the cells were collected as follows. Cells were resuspended by repeated pipetting and transferred to conical tubes. The wells and pipette were rinsed with 1 ml fresh culture medium, which was added to the initial cell suspension collected. The tube was centrifuged for 10 min at 600×g and 1 ml of supernatant was carefully collected (40% of the total supernatant) and counted for radioactivity. BSA was added as carrier protein to a final concentration of 1% and the protein was precipitated with 5 ml of cold 10% (w/v) trichloroacetic acid (TCA). After incubation for 30 min at 4° C. and centrifugation for 15 min at 5000×g, the supernatant was discarded and the precipitated protein was counted for radioactivity. The radiolabeled protein that was not precipitated by TCA was considered degraded, and precipitated radioactive protein was considered intact. The cell pellet was counted for the radioactivity remaining in the cells after being washed. Radioactivity in each fraction was expressed as a percentage of that initially bound. As shown in FIG. 8A, hLL1 showed similar rapid internalizing and catabolic manner as murine LL1 after bound to the surface of Raji cells, i.e. almost all of the bound radioactivity was catabolized and released into the supernatant within 3 h. This is much faster than with other internalizing Abs, such as anti-CD22 and anti-CD19 (Hansen et al., 1996). The studies with early time points confirmed the similar processing patterns of hLL1 and mLL1. Most catabolism was accomplished within one hour (FIG. 8B).

Example 9

Cytotoxicity of hLL1

Figure 9:
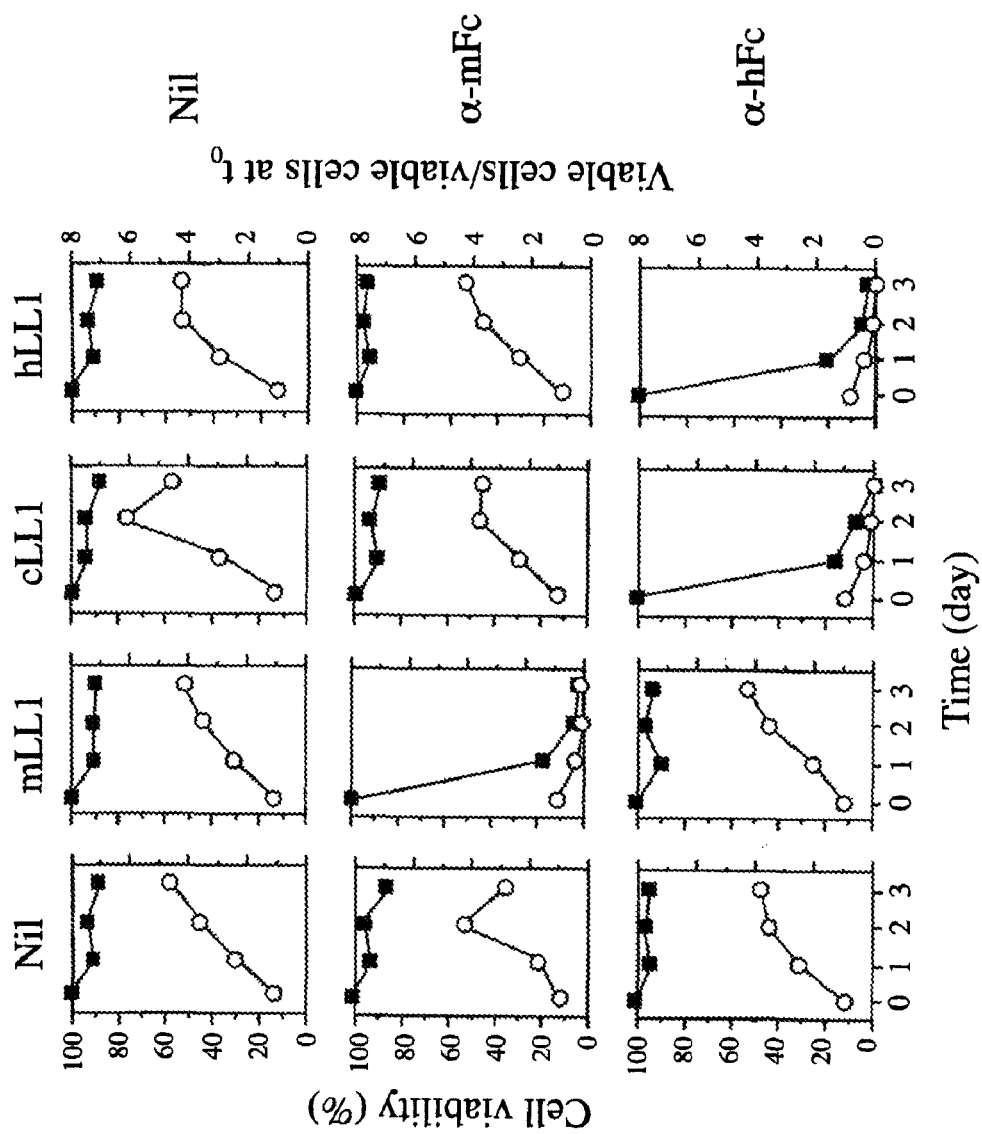
FIG. 9 shows the cytotoxicity effect of crosslinked LL1 Abs on Raji cells. $5 \times 10^5$ Raji cells were seeded at day 0 in 1 ml of culture medium containing (as indicated on top of the panels) 5 μg/ml of mLL1, cLL1 or hLL1, or no any Ab (Nil), with 50 μg/ml of -mFc or -hFc Ab, or without any crosslinker (Nil), indicated at right side of panels. The numbers of total and viable cells were counted daily for 3 days. Percentage of viable cells (squares) and the ratio of viable cells over the viable cells at time zero (diamonds) were calculated and plotted against culture time.
Figure 10:
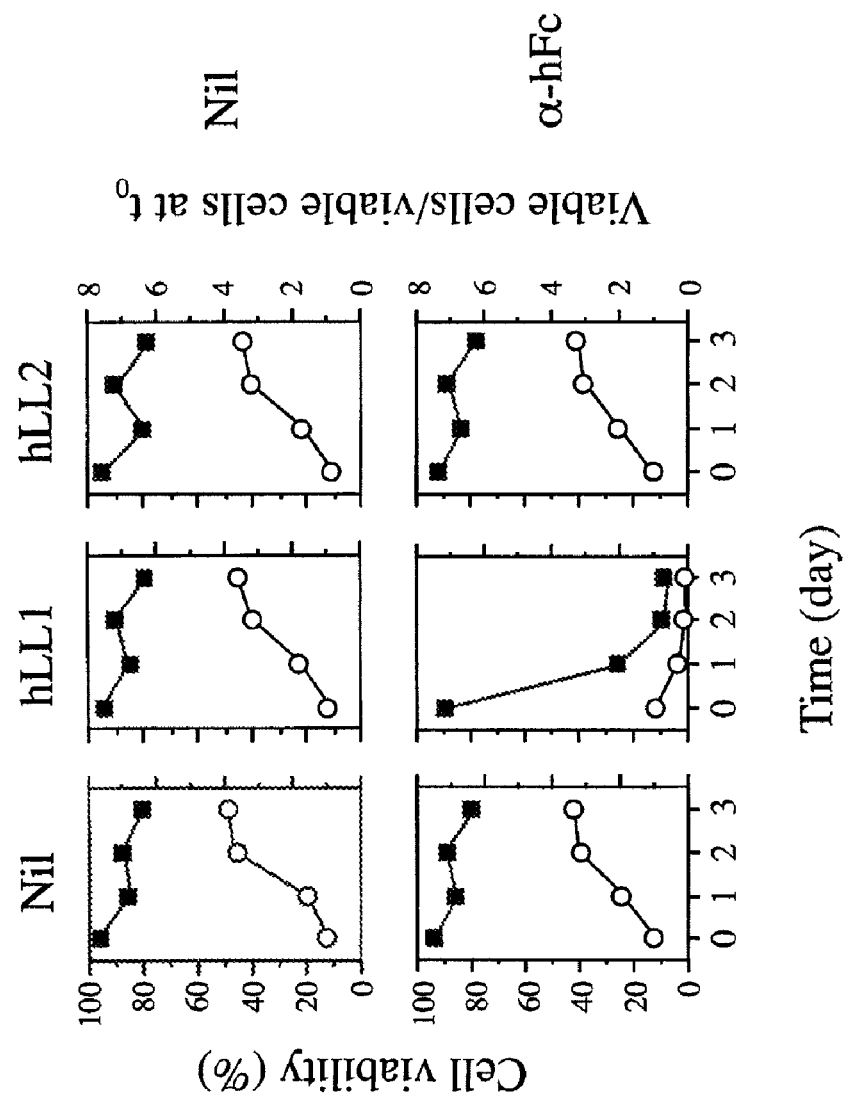
FIG. 10 shows the cytotoxicity effect of crosslinked hLL1 on Daudi cells. $5 \times 10^5$ Daudi cells were seeded at day 0 in 1 ml of culture medium containing (as indicated on top of the panels) 5 μg/ml of hLL1, or hLL2 (an anti-CD22, internalizing Ab), or no any Ab (Nil), with 50 μg/ml of -hFc Ab, or without (Nil), indicated at right side of panels. The numbers of total and viable cells were counted daily for 3 days. Percentage of viable cells (squares) and the ratio of viable cells over the viable cells at time zero (diamonds) were calculated and plotted against culture time.

The cytotoxic effect of hLL1 was compared with that of mLL1 and cLL1 in Raji cells, a human lymphoma cell line. Goat anti-human IgG Fc fragment specific Ab (α-hFc) was used as the crosslinker for hLL1 and cLL1 and goat anti-mouse IgG Fc specific Ab (α-mFc) was used for mLL1. $5 \times 10^5$ Raji cells were seeded at day 0 in 1 ml of culture medium containing 5 µg/ml of a LL1 Ab and 50 µg/ml of the appropriate crosslinker. The numbers of total and viable cells were counted daily for 3 days. As shown in FIG. 9, The total number of normal Raji cells increased 4-5 fold in 3 days and cell viability remained >80% at the end of third day. Cells treated with a crosslinker alone, a LL1 Ab alone, or a LL1 Ab with an uncomparable crosslinker (e.g. hLL1 and goat anti-mouse IgG Fc specific Ab), were indistinguishable from normal Raji cells. However, a combination of hLL1 and anti-human IgG Fc specific Ab effectively caused cell death: >40% reduction in cell viability in one day and almost total cell death in 3 days. The effectiveness of hLL1 was comparable with that of mLL1 and cLL1. Similar results were observed when Daudi cells were used (FIG. 10). No such effect was observed with another internalizing Ab, hLL2, (humanized anti-CD22 Ab). These results demonstrated that the cytotoxicity effect of hLL1 on lymphoma cell lines is specifically dependent on crosslinking of the Ab on cell surface.

SEQUENCE LISTING

```
<160> NUMBER OF SEQ ID NOS: 33

<210> SEQ ID NO 1
<211> LENGTH: 360
<212> TYPE: DNA
<213> ORGANISM: Mus sp.
<220> FEATURE:
<221> NAME/KEY: CDS
<222> LOCATION: (1)..(360)

<400> SEQUENCE: 1 cag atc cag ttg gtg cag tct gga cct gag ctg aag aag cct gga gag      48
Gln Ile Gln Leu Val Gln Ser Gly Pro Glu Leu Lys Lys Pro Gly Glu
 1               5                  10                  15 aca gtc aag gtc acc tgc aag act tct gga tat acc ttc aca aac tat      96
Thr Val Lys Val Thr Cys Lys Thr Ser Gly Tyr Thr Phe Thr Asn Tyr
            20                  25                  30
```

```
gga gtg aac tgg ata aag cag act cca gga gag ggt tta cag tgg atg      144
Gly Val Asn Trp Ile Lys Gln Thr Pro Gly Glu Gly Leu Gln Trp Met
         35                  40                  45 ggc tgg ata aac ccc aac act gga gag cca aca ttt gat gat gac ttc      192
Gly Trp Ile Asn Pro Asn Thr Gly Glu Pro Thr Phe Asp Asp Asp Phe
 50                  55                  60 aag gga cga ttt gcc ttc tct ttg gaa tcc tct gcc agc act gcc ttt      240
Lys Gly Arg Phe Ala Phe Ser Leu Glu Ser Ser Ala Ser Thr Ala Phe
 65                  70                  75                  80 ttg cag atc agc aac ctc aaa aat gag gac atg ggt aca tat ttc tgt      288
Leu Gln Ile Ser Asn Leu Lys Asn Glu Asp Met Gly Thr Tyr Phe Cys
                 85                  90                  95 tca aga tcg agg ggt aaa aac gaa gcc tgg ttt gct tat tgg ggc caa      336
Ser Arg Ser Arg Gly Lys Asn Glu Ala Trp Phe Ala Tyr Trp Gly Gln
            100                 105                 110 ggg act ctg gtc act gtc tct gaa                                      360
Gly Thr Leu Val Thr Val Ser Glu
        115                 120

<210> SEQ ID NO 2
<211> LENGTH: 120
<212> TYPE: PRT
<213> ORGANISM: Mus sp.

<400> SEQUENCE: 2

Gln Ile Gln Leu Val Gln Ser Gly Pro Glu Leu Lys Lys Pro Gly Glu
 1               5                  10                  15

Thr Val Lys Val Thr Cys Lys Thr Ser Gly Tyr Thr Phe Thr Asn Tyr
             20                  25                  30

Gly Val Asn Trp Ile Lys Gln Thr Pro Gly Glu Gly Leu Gln Trp Met
         35                  40                  45

Gly Trp Ile Asn Pro Asn Thr Gly Glu Pro Thr Phe Asp Asp Asp Phe
 50                  55                  60

Lys Gly Arg Phe Ala Phe Ser Leu Glu Ser Ser Ala Ser Thr Ala Phe
 65                  70                  75                  80

Leu Gln Ile Ser Asn Leu Lys Asn Glu Asp Met Gly Thr Tyr Phe Cys
                 85                  90                  95

Ser Arg Ser Arg Gly Lys Asn Glu Ala Trp Phe Ala Tyr Trp Gly Gln
            100                 105                 110

Gly Thr Leu Val Thr Val Ser Glu
        115                 120

<210> SEQ ID NO 3
<211> LENGTH: 337
<212> TYPE: DNA
<213> ORGANISM: Mus sp.
<220> FEATURE:
<221> NAME/KEY: CDS
<222> LOCATION: (1)..(333)

<400> SEQUENCE: 3 gat gtt gtg atg acc caa act cca ctc tcc ctg cct gtc agt ctt gga      48
Asp Val Val Met Thr Gln Thr Pro Leu Ser Leu Pro Val Ser Leu Gly
 1               5                  10                  15 gat caa gcc tcc atc tct tgc aga tct agt cag agc ctt gta cac aga      96
Asp Gln Ala Ser Ile Ser Cys Arg Ser Ser Gln Ser Leu Val His Arg
             20                  25                  30 aat gga aac acc tat tta cat tgg tac ctg cag aag cca ggc cag tct     144
Asn Gly Asn Thr Tyr Leu His Trp Tyr Leu Gln Lys Pro Gly Gln Ser
         35                  40                  45
```

```
cca aag ctc ctg atc tac aca gtt tcc aac cga ttt tct ggg gtc cca      192
Pro Lys Leu Leu Ile Tyr Thr Val Ser Asn Arg Phe Ser Gly Val Pro
    50                  55                  60 gac agg ttc agt ggc agt gga tca ggg aca gat ttc aca ctc aag atc      240
Asp Arg Phe Ser Gly Ser Gly Ser Gly Thr Asp Phe Thr Leu Lys Ile
65                  70                  75                  80 agt aga gtg gag gct gag gat ctg gga ctt tat ttc tgc tct caa agt      288
Ser Arg Val Glu Ala Glu Asp Leu Gly Leu Tyr Phe Cys Ser Gln Ser
                85                  90                  95 tca cat gtt cct ccc acg ttc ggt gct ggg acc aag ctg gag atc taac    337
Ser His Val Pro Pro Thr Phe Gly Ala Gly Thr Lys Leu Glu Ile
            100                 105                 110

<210> SEQ ID NO 4
<211> LENGTH: 111
<212> TYPE: PRT
<213> ORGANISM: Mus sp.

<400> SEQUENCE: 4

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Arg
                20                  25                  30

Asn Gly Asn Thr Tyr Leu His Trp Tyr Leu Gln Lys Pro Gly Gln Ser
            35                  40                  45

Pro Lys Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Phe Cys Ser Gln Ser
                85                  90                  95

Ser His Val Pro Pro Thr Phe Gly Ala Gly Thr Lys Leu Glu Ile
            100                 105                 110

<210> SEQ ID NO 5
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(360)

<400> SEQUENCE: 5 cag gtc caa ctg cag cag tct gga cct gag ctg aag aag cct gga gag       48
Gln Val Gln Leu Gln Gln Ser Gly Pro Glu Leu Lys Lys Pro Gly Glu
1               5                   10                  15 aca gtc aag gtc acc tgc aag act tct gga tat acc ttc aca aac tat      96
Thr Val Lys Val Thr Cys Lys Thr Ser Gly Tyr Thr Phe Thr Asn Tyr
                20                  25                  30 gga gtg aac tgg ata aag cag act cca gga gag ggt tta cag tgg atg     144
Gly Val Asn Trp Ile Lys Gln Thr Pro Gly Glu Gly Leu Gln Trp Met
            35                  40                  45 ggc tgg ata aac ccc aac act gga gag cca aca ttt gat gat gac ttc     192
Gly Trp Ile Asn Pro Asn Thr Gly Glu Pro Thr Phe Asp Asp Asp Phe
    50                  55                  60 aag gga cga ttt gcc ttc tct ttg gaa tcc tct gcc agc act gcc ttt     240
Lys Gly Arg Phe Ala Phe Ser Leu Glu Ser Ser Ala Ser Thr Ala Phe
65                  70                  75                  80 ttg cag atc agc aac ctc aaa aat gag gac atg ggt aca tat ttc tgt     288
```

```
Leu Gln Ile Ser Asn Leu Lys Asn Glu Asp Met Gly Thr Tyr Phe Cys
                85                  90                  95 tca aga tcg agg ggt aaa aac gaa gcc tgg ttt gct tat tgg ggc caa         336
Ser Arg Ser Arg Gly Lys Asn Glu Ala Trp Phe Ala Tyr Trp Gly Gln
                100                 105                 110 ggg act ctg gtc acc gtc tcc tca                                         360
Gly Thr Leu Val Thr Val Ser Ser
        115                 120

<210> SEQ ID NO 6
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Val Gln Leu Gln Gln Ser Gly Pro Glu Leu Lys Lys Pro Gly Glu
1               5                   10                  15

Thr Val Lys Val Thr Cys Lys Thr Ser Gly Tyr Thr Phe Thr Asn Tyr
                20                  25                  30

Gly Val Asn Trp Ile Lys Gln Thr Pro Gly Glu Gly Leu Gln Trp Met
            35                  40                  45

Gly Trp Ile Asn Pro Asn Thr Gly Glu Pro Thr Phe Asp Asp Asp Phe
        50                  55                  60

Lys Gly Arg Phe Ala Phe Ser Leu Glu Ser Ser Ala Ser Thr Ala Phe
65                  70                  75                  80

Leu Gln Ile Ser Asn Leu Lys Asn Glu Asp Met Gly Thr Tyr Phe Cys
                85                  90                  95

Ser Arg Ser Arg Gly Lys Asn Glu Ala Trp Phe Ala Tyr Trp Gly Gln
                100                 105                 110

Gly Thr Leu Val Thr Val Ser Ser
        115                 120

<210> SEQ ID NO 7
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(339)

<400> SEQUENCE: 7 gac atc cag ctg acc caa act cca ctc tcc ctg cct gtc agt ctt gga         48
Asp Ile Gln Leu Thr Gln Thr Pro Leu Ser Leu Pro Val Ser Leu Gly
1               5                   10                  15 gat caa gcc tcc atc tct tgc aga tct agt cag agc ctt gta cac aga         96
Asp Gln Ala Ser Ile Ser Cys Arg Ser Ser Gln Ser Leu Val His Arg
                20                  25                  30 aat gga aac acc tat tta cat tgg tac ctg cag aag cca ggc cag tct        144
Asn Gly Asn Thr Tyr Leu His Trp Tyr Leu Gln Lys Pro Gly Gln Ser
            35                  40                  45 cca aag ctc ctg atc tac aca gtt tcc aac cga ttt tct ggg gtc cca        192
Pro Lys Leu Leu Ile Tyr Thr Val Ser Asn Arg Phe Ser Gly Val Pro
        50                  55                  60 gac agg ttc agt ggc agt gga tca ggg aca gat ttc aca ctc aag atc        240
Asp Arg Phe Ser Gly Ser Gly Ser Gly Thr Asp Phe Thr Leu Lys Ile
65                  70                  75                  80
```

```
agt aga gtg gag gct gag gat ctg gga ctt tat ttc tgc tct caa agt      288
Ser Arg Val Glu Ala Glu Asp Leu Gly Leu Tyr Phe Cys Ser Gln Ser
            85                  90                  95 tca cat gtt cct ccc acg ttc ggt gct ggg acc aag ctg gag atc aaa      336
Ser His Val Pro Pro Thr Phe Gly Ala Gly Thr Lys Leu Glu Ile Lys
        100                 105                 110 cgt                                                                   339
Arg
```

<210> SEQ ID NO 8
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Leu Thr Gln Thr Pro Leu Ser Leu Pro Val Ser Leu Gly
1               5                   10                  15

Asp Gln Ala Ser Ile Ser Cys Arg Ser Ser Gln Ser Leu Val His Arg
            20                  25                  30

Asn Gly Asn Thr Tyr Leu His Trp Tyr Leu Gln Lys Pro Gly Gln Ser
        35                  40                  45

Pro Lys Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Phe Cys Ser Gln Ser
                85                  90                  95

Ser His Val Pro Pro Thr Phe Gly Ala Gly Thr Lys Leu Glu Ile Lys
            100                 105                 110

Arg

<210> SEQ ID NO 9
<211> LENGTH: 120
<212> TYPE: PRT
<213> ORGANISM: Homo sapiens

<400> SEQUENCE: 9

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Asp Asp Thr Ala Val Tyr Tyr Cys
                85                  90                  95

Ala Arg Glu Asp Ser Asn Gly Tyr Lys Ile Phe Asp Tyr Trp Gly Gln
            100                 105                 110

Gly Ser Leu Val Thr Val Ser Ser
        115                 120

<210> SEQ ID NO 10
<211> LENGTH: 360

```
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(360)

<400> SEQUENCE: 10 cag gtc caa ctg cag caa tct ggg tct gag ttg aag aag cct ggg gcc      48
Gln Val Gln Leu Gln Gln Ser Gly Ser Glu Leu Lys Lys Pro Gly Ala
 1               5                  10                  15 tca gtg aag gtt tcc tgc aag gct tct gga tac acc ttc act aac tat      96
Ser Val Lys Val Ser Cys Lys Ala Ser Gly Tyr Thr Phe Thr Asn Tyr
             20                  25                  30 gga gtg aac tgg ata aag cag gcc cct gga caa ggg ctt cag tgg atg     144
Gly Val Asn Trp Ile Lys Gln Ala Pro Gly Gln Gly Leu Gln Trp Met
         35                  40                  45 ggc tgg ata aac ccc aac act gga gag cca aca ttt gat gat gac ttc     192
Gly Trp Ile Asn Pro Asn Thr Gly Glu Pro Thr Phe Asp Asp Asp Phe
     50                  55                  60 aag gga cga ttt gcc ttc tcc ttg gac acc tct gtc agc acg gca tat     240
Lys Gly Arg Phe Ala Phe Ser Leu Asp Thr Ser Val Ser Thr Ala Tyr
 65                  70                  75                  80 ctc cag atc agc agc cta aag gct gac gac act gcc gtg tat ttc tgt     288
Leu Gln Ile Ser Ser Leu Lys Ala Asp Asp Thr Ala Val Tyr Phe Cys
                 85                  90                  95 tca aga tcg agg ggt aaa aac gaa gcc tgg ttt gct tat tgg ggc caa     336
Ser Arg Ser Arg Gly Lys Asn Glu Ala Trp Phe Ala Tyr Trp Gly Gln
            100                 105                 110 ggg agc ctg gtc acc gtc tcc tca                                     360
Gly Ser Leu Val Thr Val Ser Ser
        115                 120

<210> SEQ ID NO 11
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Gln Gln Ser Gly Ser Glu Leu Lys Lys Pro Gly Ala
 1               5                  10                  15

Ser Val Lys Val Ser Cys Lys Ala Ser Gly Tyr Thr Phe Thr Asn Tyr
             20                  25                  30

Gly Val Asn Trp Ile Lys Gln Ala Pro Gly Gln Gly Leu Gln Trp Met
         35                  40                  45

Gly Trp Ile Asn Pro Asn Thr Gly Glu Pro Thr Phe Asp Asp Asp Phe
     50                  55                  60

Lys Gly Arg Phe Ala Phe Ser Leu Asp Thr Ser Val Ser Thr Ala Tyr
 65                  70                  75                  80

Leu Gln Ile Ser Ser Leu Lys Ala Asp Asp Thr Ala Val Tyr Phe Cys
                 85                  90                  95

Ser Arg Ser Arg Gly Lys Asn Glu Ala Trp Phe Ala Tyr Trp Gly Gln
            100                 105                 110

Gly Ser Leu Val Thr Val Ser Ser
        115                 120

<210> SEQ ID NO 12
```

<211> LENGTH: 111
<212> TYPE: PRT
<213> ORGANISM: Homo sapiens

<400> SEQUENCE: 12

```
Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val His Ser
             20                  25                  30

Asp Gly Asn Thr Tyr Leu Asn Trp Phe Gln Gln Arg Pro Gly Gln Ser
         35                  40                  45

Pro Arg Arg Leu Ile Tyr Lys Val Ser Asn Arg Asp Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Thr His Trp Pro Phe Thr Phe Gly Gln Gly Thr Arg Leu Glu Ile
            100                 105                 110
```

<210> SEQ ID NO 13
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(339)

<400> SEQUENCE: 13

```
gac atc cag ctg act cag tct cca ctc tcc ctg ccc gtc acc ctt gga      48
Asp Ile Gln Leu Thr Gln Ser Pro Leu Ser Leu Pro Val Thr Leu Gly
 1               5                  10                  15 cag ccg gcc tcc atc tcc tgc aga tca agt cag agc ctt gta cac aga      96
Gln Pro Ala Ser Ile Ser Cys Arg Ser Ser Gln Ser Leu Val His Arg
             20                  25                  30 aat gga aac acc tat tta cat tgg ttt cag cag agg cca ggc caa tct    144
Asn Gly Asn Thr Tyr Leu His Trp Phe Gln Gln Arg Pro Gly Gln Ser
         35                  40                  45 cca agg ctc ctg atc tac aca gtt tcc aac cga ttt tct ggg gtc cca    192
Pro Arg Leu Leu Ile Tyr Thr Val Ser Asn Arg Phe Ser Gly Val Pro
     50                  55                  60 gac aga ttc agc ggc agt ggg tca ggc act gat ttc aca ctg aaa atc    240
Asp Arg Phe Ser Gly Ser Gly Ser Gly Thr Asp Phe Thr Leu Lys Ile
 65                  70                  75                  80 agc agg gtg gag gct gag gat gtt ggg gtt tat ttc tgc tct caa agt    288
Ser Arg Val Glu Ala Glu Asp Val Gly Val Tyr Phe Cys Ser Gln Ser
                 85                  90                  95 tca cat gtt cct ccc acg ttc ggt gct ggg aca cga ctg gag atc aaa    336
Ser His Val Pro Pro Thr Phe Gly Ala Gly Thr Arg Leu Glu Ile Lys
            100                 105                 110 cgt                                                                 339
Arg
```

<210> SEQ ID NO 14
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 14

Asp Ile Gln Leu Thr Gln Ser Pro Leu Ser Leu Pro Val Thr Leu Gly
1               5                   10                  15

Gln Pro Ala Ser Ile Ser Cys Arg Ser Ser Gln Ser Leu Val His Arg
            20                  25                  30

Asn Gly Asn Thr Tyr Leu His Trp Phe Gln Gln Arg Pro Gly Gln Ser
        35                  40                  45

Pro Arg Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Ser His Val Pro Pro Thr Phe Gly Ala Gly Thr Arg Leu Glu Ile Lys
            100                 105                 110

Arg

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Gly Gly Ser
1

<210> SEQ ID NO 16
<211> LENGTH: 16
<212> TYPE: PRT
<213> ORGANISM: Mus sp.

<400> SEQUENCE: 16

Arg Ser Ser Gln Ser Leu Val His Arg Asn Gly Asn Thr Tyr Leu His
1               5                   10                  15

<210> SEQ ID NO 17
<211> LENGTH: 7
<212> TYPE: PRT
<213> ORGANISM: Mus sp.

<400> SEQUENCE: 17

Thr Val Ser Asn Arg Phe Ser
1               5

<210> SEQ ID NO 18
<211> LENGTH: 9
<212> TYPE: PRT
<213> ORGANISM: Mus sp.

<400> SEQUENCE: 18

Ser Gln Ser Ser His Val Pro Pro Thr
1               5

<210> SEQ ID NO 19
<211> LENGTH: 5
<212> TYPE: PRT
<213> ORGANISM: Mus sp.

<400> SEQUENCE: 19

Asn Tyr Gly Val Asn
1               5

<210> SEQ ID NO 20
<211> LENGTH: 17
<212> TYPE: PRT
<213> ORGANISM: Mus sp.

<400> SEQUENCE: 20

Trp Ile Asn Pro Asn Thr Gly Glu Pro Thr Phe Asp Asp Asp Phe Lys
1               5                   10                  15

Gly

<210> SEQ ID NO 21
<211> LENGTH: 11
<212> TYPE: PRT
<213> ORGANISM: Mus sp.

<400> SEQUENCE: 21

Ser Arg Gly Lys Asn Glu Ala Trp Phe Ala Tyr
1               5                   10

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Gly Gly Gly Ser Gly Gly Gly Gly Ser Gly Gly Gly Gly Ser
1               5                   10                  15

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gatgttcagc tgacccaaac tccactctcc                                    30

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cagatccagc tgcagcagtc tggacctgag                                    30

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gagacggtga ccagagtccc ttggccccaa                                    30

```
<210> SEQ ID NO 26
<211> LENGTH: 176
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
ggtctgagtt gaagaagcct ggggcctcag tgaaggtttc ctgcaaggct tctggataca        60
ccttcactaa ctatggagtg aactggataa agcaggcccc tggacaaggg cttcagtgga       120
tgggctggat aaaccccaac actggagagc aacatttga tgatgacttc aaggga           176

<210> SEQ ID NO 27
<211> LENGTH: 165
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
tcccttggcc ccaataagca aaccaggctt cgttttacc cctcgatctt gaacagaaat         60
acacggcagt gtcgtcagcc tttaggctgc tgatctggag atatgccgtg ctgacagagg       120
tgtccaagga gaaggcaaat cgtcccttga agtcatcatc aaatg                      165

<210> SEQ ID NO 28
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gtggtgctgc agcaatctgg gtctgagttc aagaagct                                38

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
aagtggatcc tataatcatt cctaggatta atg                                    33

<210> SEQ ID NO 30
<211> LENGTH: 159
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
cagtctccac tctccctgcc cgtcacccct ggacagccgg cctccatctc ctgcagatca        60
agtcagagcc ttgtacacag aaatggaaac acctatttac attggtttca gcagaggcca      120
ggccaatctc caaggctcct gatctacaca gtttccaac                             159

<210> SEQ ID NO 31
```

```
<211> LENGTH: 169
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
tgtcccagca ccgaacgtgg gaggaacatg tgaactttga gagcagaaat aaacccccaac     60 atcctcagcc tccaccctgc tgattttcag tgtgaaatca gtgcctgacc cactgccgct    120
gaatctgtct gggaccccag aaaatcggtt ggaaactgtg tagatcagg                169

<210> SEQ ID NO 32
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gatgttcagc tgactcagtc tccactctcc ctg                                   33

<210> SEQ ID NO 33
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gttagatctc cagtcgtgtc ccagcaccga acg                                   33
```

What is claimed is:

1. A method of delivering a therapeutic or diagnostic agent to a target cell that expresses CD74 comprising:
   a) exposing the target cell to a humanized anti-CD74 antibody or antigen binding fragment thereof, wherein said antibody or fragment thereof:
      (i) is internalized by Raji lymphoma cells in culture;
      (ii) induces apoptosis of Raji cells in cell culture when cross-linked with goat antisera reactive with the Fc of a human IgG;
      (iii) competes for binding to CD74 with, or binds to the same epitope of CD74 as, an anti-CD74 antibody comprising the light chain complementarity-determining region (CDR) sequences CDR1 (RSSQSLVHRNGNTYLH; SEQ ID NO:16), CDR2 (TVSNRFS; SEQ ID NO:17), and CDR3 (SQSSHVPPT; SEQ ID NO:18) and the heavy chain CDR sequences CDR1 (NYGVN; SEQ ID NO:19), CDR2 (WINPNTGEPTFDDDFKG; SEQ ID NO:20), and CDR3 (SRGKNEAWFAY; SEQ ID NO:21);
   wherein said humanized anti-CD74 antibody or fragment thereof is attached to at least one diagnostic or therapeutic agent.

2. The method of claim 1, wherein said humanized anti-CD74 antibody or fragment thereof competes for binding to CD74 with an anti-CD74 antibody comprising the light chain complementarity-determining region (CDR) sequences CDR1 (RSSQSLVHRNGNTYLH; SEQ ID NO:16), CDR2 (TVSNRFS; SEQ ID NO:17), and CDR3 (SQSSHVPPT; SEQ ID NO:18) and the heavy chain CDR sequences CDR1 (NYGVN; SEQ ID NO:19), CDR2 (WINPNTGEPTFDDDFKG; SEQ ID NO:20), and CDR3 (SRGKNEAWFAY; SEQ ID NO:21).

3. The method of claim 1, wherein said humanized anti-CD74 antibody or fragment thereof binds to the same epitope of CD74 as an anti-CD74 antibody comprising the light chain complementarity-determining region (CDR) sequences CDR1 (RSSQSLVHRNGNTYLH; SEQ ID NO:16), CDR2 (TVSNRFS; SEQ ID NO:17), and CDR3 (SQSSHVPPT; SEQ ID NO:18) and the heavy chain CDR sequences CDR1 (NYGVN; SEQ ID NO:19), CDR2 (WINPNTGEPTFDDDFKG; SEQ ID NO:20), and CDR3 (SRGKNEAWFAY; SEQ ID NO:21).

4. The method of claim 1, wherein the target cell is a cancer cell selected from the group consisting of a solid tumor, non-Hodgkin's lymphoma, Hodgkin's lymphoma, multiple myeloma, a B cell malignancy, a T cell malignancy, a melanoma, a carcinoma, a sarcoma, renal carcinoma, lung carcinoma, intestinal carcinoma, stomach carcinoma, indolent B cell lymphoma, aggressive B-cell lymphoma, chronic lymphatic leukemia and acute lymphatic leukemia.

5. The method of claim 1, wherein the target cell is a B cell or a T cell.

6. The method of claim 1, wherein the therapeutic agent is selected from the group consisting of a second antibody or fragment thereof, an immunoconjugate, an immunomodulator, a hormone, a cytotoxic agent, an enzyme, an antisense oligonucleotide, a boron compound, a photoactive agent and a radionuclide.

7. The method of claim 6, wherein the cytotoxic agent is a drug or toxin.

8. The method of claim 6, wherein the immunomodulator is selected from the group consisting of a cytokine, a stem cell growth factor, a lymphotoxin, a tumor necrosis factor, a hematopoietic factor, a colony stimulating factor, an interferon, erythropoietin, thrombopoietin, or a combination thereof.

9. The method of claim 8, wherein the hematopoietic factor is an interleukin selected from the group consisting of IL-1, IL-2, IL-3, IL-6, IL-10, IL-12, IL-18 and IL-21.

10. The method of claim 8, wherein the colony stimulating factor is granulocyte-colony stimulating factor (G-CSF) or granulocyte macrophage-colony stimulating factor (GM-CSF).

11. The method of claim 6, wherein the radionuclide is selected from the group consisting of $^{225}$Ac, $^{18}$F, $^{68}$Ga, $^{67}$Ga, $^{90}$Y, $^{86}$Y, $^{111}$In, $^{131}$I, $^{125}$I, $^{123}$I, $^{99m}$Tc, $^{94m}$Tc, $^{186}$Re, $^{188}$Re, $^{177}$Lu, $^{62}$Cu, $^{64}$Cu, $^{67}$Cu, $^{212}$Bi, $^{213}$Bi, $^{32}$P, $^{11}$C, $^{13}$N, $^{15}$O, $^{76}$Br, and $^{211}$At.

12. The method of claim 6, wherein the second antibody binds to an antigen selected from the group consisting of CD4, CD5, CD8, CD14, CD15, CD19, CD20, CD21, CD22, CD23, CD25, CD30, CD33, CD37, CD38, CD40, CD40L, CD46, CD52, CD54, CD74, CD80, CD126, B7, MUC-1, Ia, tenascin, HM1.24 and HLA-DR.

13. The method of claim 1, wherein the therapeutic agent is selected from the group consisting of vinca alkaloids, anthracyclines, epipodophyllotoxins, taxanes, antimetabolites, alkylating agents, antibiotics, COX-2 inhibitors, antimitotics, antiangiogenic agents, apoptotic agents, doxorubicin, methotrexate, taxol, CPT-11, camptothecins, nitrogen mustards, alkyl sulfonates, nitrosoureas, triazenes, folic acid analogs, COX-2 inhibitors, pyrimidine analogs, purine analogs, platinum coordination complexes, cyclophosphamide, etoposide, carmustine, vincristine, procarbazine, prednisone, methotrexate, bleomycin, dexamethasone, leucovorin, phenyl butyrate, bryostatin-1 and hormones.

14. The method of claim 7, wherein the toxin is selected from the group consisting of ricin, abrin, DNase I, *Staphylococcal* enterotoxin-A, pokeweed antiviral protein, gelonin, diphtheria toxin, *Pseudomonas* exotoxin, and *Pseudomonas* endotoxin.

15. The method of claim 1, wherein said humanized anti-CD74 antibody or fragment thereof comprises human IgG1, IgG2a, IgG3 or IgG4 constant regions.

16. The method of claim 1, wherein said humanized anti-CD74 antibody fragment is selected from the group consisting of a F(ab')$_2$, F(ab'), Fab, scFv and Fv fragment.

17. The method of claim 1, wherein said humanized anti-CD74 antibody or fragment thereof is a fusion protein.

18. The method of claim 1, wherein said target cell is exposed to said humanized anti-CD74 antibody or fragment thereof by administering the antibody or fragment thereof to a subject in vivo.

19. The method of claim 1, wherein said target cell is exposed to said humanized anti-CD74 antibody or fragment thereof in vitro.

20. The method of claim 1, wherein said diagnostic agent is selected from the group consisting of a radioisotope, a dye, a contrast agent, a fluorescent agent, an enhancing agent and a paramagnetic ion.

21. The method of claim 20, wherein the radioisotope is selected from the group consisting of $^{125}$I, $^{131}$I, $^{123}$I, $^{124}$I, $^{62}$Cu, $^{64}$Cu, $^{18}$F, $^{111}$In, $^{67}$Ga, $^{68}$Ga, $^{99m}$Tc, $^{94m}$Tc, $^{11}$C, $^{13}$N, $^{15}$O and $^{76}$Br.

22. A method for treating a cancer, comprising:

a) administering to a subject a humanized anti-CD74 antibody or antigen binding fragment thereof, wherein said antibody or fragment thereof:
  (i) is internalized by Raji lymphoma cells in culture;
  (ii) induces apoptosis of Raji cells in cell culture when cross-linked with goat antisera reactive with the Fc of a human IgG; and
  (iii) competes for binding to CD74 with, or binds to the same epitope of CD74 as, an anti-CD74 antibody comprising the light chain complementarity-determining region (CDR) sequences CDR1 (RSSQSLVHRNGNTYLH; SEQ ID NO:16), CDR2 (TVSNRFS; SEQ ID NO:17), and CDR3 (SQSSHVPPT; SEQ ID NO:18) and the heavy chain CDR sequences CDR1 (NYGVN; SEQ ID NO:19), CDR2 (WINPNTGEPTFDDDFKG; SEQ ID NO:20), and CDR3 (SRGKNEAWFAY; SEQ ID NO:21).

23. The method of claim 22, wherein the humanized anti-CD74 antibody is a naked antibody.

24. The method of claim 23, wherein said naked anti-CD74 antibody is effective to treat cancer in the absence of any other administered antibody or antibody fragment.

25. The method of claim 24, wherein the cancer is selected from the group consisting of a solid tumor, non-Hodgkin's lymphoma, Hodgkin's lymphoma, multiple myeloma, a B-cell malignancy, a T-cell malignancy, a melanoma, a carcinoma, a sarcoma, renal carcinoma, lung carcinoma, intestinal carcinoma, stomach carcinoma, indolent B-cell lymphoma, aggressive B-cell lymphoma, chronic lymphatic leukemia and acute lymphatic leukemia.

26. The method of claim 25, wherein the solid tumor is selected from the group consisting of a melanoma, carcinoma and sarcoma.

27. The method of claim 26, wherein the carcinoma is selected from the group consisting of renal carcinoma, lung carcinoma, intestinal carcinoma and stomach carcinoma.

28. The method of claim 22, wherein the humanized anti-CD74 antibody or fragment thereof is conjugated to at least one therapeutic agent.

29. The method of claim 28, wherein the therapeutic agent is therapeutic agent is selected from the group consisting of a second antibody or fragment thereof, an immunoconjugate, an immunomodulator, a hormone, a cytotoxic agent, an enzyme, an antisense oligonucleotide, a boron compound, a photoactive agent and a radionuclide.

30. The method of claim 29, wherein the cytotoxic agent is a drug or toxin.

31. The method of claim 22, further comprising administering at least one therapeutic agent to said subject.

32. The method of claim 31, wherein the therapeutic agent is therapeutic agent is selected from the group consisting of a second antibody or fragment thereof, an immunoconjugate, an immunomodulator, a hormone, a cytotoxic agent, an enzyme, an antisense oligonucleotide, a boron compound, a photoactive agent and a radionuclide.

33. The method of claim 22, wherein the humanized anti-CD74 antibody or fragment thereof is a fusion protein.

34. The method of claim 22, wherein the humanized anti-CD74 antibody or fragment thereof is a bispecific antibody or fragment thereof.

35. The method of claim 34, wherein the bispecific antibody comprises at least one hapten-binding site.

36. The method of claim 35, further comprising administering to the subject a targetable conjugate comprising at least one hapten and at least one therapeutic agent.

37. The method of claim 36, wherein the therapeutic agent is therapeutic agent is selected from the group consisting of a second antibody or fragment thereof, an immunoconjugate, an immunomodulator, a hormone, a cytotoxic agent, an enzyme, an antisense oligonucleotide, a boron compound, a photoactive agent and a radionuclide.

38. The method of claim 22, wherein the humanized anti-CD74 antibody or fragment thereof is a multispecific antibody or fragment thereof.

* * * * *